United States Patent
Rengifo

(10) Patent No.: US 9,428,759 B2
(45) Date of Patent: Aug. 30, 2016

(54) **METHODS FOR INCREASING THE PRODUCTION OF PHENOLIC COMPOUNDS FROM *THEOBROMA CACAO***

(71) Applicant: Raul Cuero Rengifo, Cypress, TX (US)

(72) Inventor: Raul Cuero Rengifo, Cypress, TX (US)

(73) Assignee: Casa Luker S.A., Bogota (CO)

( * ) Notice: Subject to any disclaimer, the term of this patent is extended or adjusted under 35 U.S.C. 154(b) by 484 days.

(21) Appl. No.: 13/951,619

(22) Filed: Jul. 26, 2013

(65) Prior Publication Data

US 2014/0033360 A1     Jan. 30, 2014

Related U.S. Application Data

(60) Provisional application No. 61/675,869, filed on Jul. 26, 2012.

(51) Int. Cl.
*C12N 9/88* (2006.01)
*C12N 15/82* (2006.01)

(52) U.S. Cl.
CPC ............ *C12N 15/8243* (2013.01); *C12N 9/88* (2013.01)

(58) Field of Classification Search
CPC ... C12N 15/8243; A61K 31/05; A01N 43/40
See application file for complete search history.

(56) References Cited

U.S. PATENT DOCUMENTS

| | | | |
|---|---|---|---|
| 6,150,587 A * | 11/2000 | Guiltinan et al. ..... | A01H 4/001 435/419 |
| 6,551,795 B1 | 4/2003 | Rubenfield | |
| 2002/0160378 A1 | 10/2002 | Harper | |
| 2003/0163837 A1 | 8/2003 | Aldwinckle | |
| 2005/0053951 A1 | 3/2005 | Breaker | |
| 2007/0048855 A1 | 3/2007 | Gamez | |
| 2009/0038023 A1 | 2/2009 | Weiner | |
| 2009/0158456 A1 | 6/2009 | Tanksley | |
| 2012/0135486 A1 | 5/2012 | Reppas | |
| 2012/0180160 A1 | 7/2012 | Shah | |

FOREIGN PATENT DOCUMENTS

WO     02068579     9/2002

OTHER PUBLICATIONS

Daayf, F., et al. "Elicitation of soluble phenolics in date palm (Phoenix dactylifera) callus by *Fusarium oxysporum* f. sp. albedinis culture medium." Environmental and Experimental Botany 49.1 (2003): 41-47.*

Maachia, Sihem Ben, et al. 2010, "Bacillus Induces Phenolic Compounds and Enhances Resistance to Uncinula necator Infection in Grapevine Leaves." The African Journal of Plant Science and Biotechnology, 4 (Special Issue 2), 46-53.*

(Continued)

*Primary Examiner* — Russell Kallis
*Assistant Examiner* — Weihua Fan
(74) *Attorney, Agent, or Firm* — Gardner Groff Greenwald & Villanueva, PC

(57) ABSTRACT

Described herein are methods for enhancing the production of phenolic compounds from *Theobroma cacao*. For example, the devices and methods described herein increase the production of phenolic compounds from cocoa plants, which has industrial and economic value. The phenolic compounds produced by the devices and methods do not require the ultra purification that is common in conventional or commercial methods. The devices and methods described herein also enhance the growth rate of plants.

15 Claims, 6 Drawing Sheets

(56) References Cited

OTHER PUBLICATIONS

Pancaningtyas, Sulistyani. "Study on the presence and influence of phenolic compounds in callogenesis and somatic embryo development of cocoa (*Theobroma cacao* L.)." Pelita Perkebunan (Coffee and Cocoa Research Journal) 31.1 (2015): 14-20.*

Cuero et al., "Constructed molecular sensor to enhance metal detection by bacterial ribosomal switch-ion channel protein interaction," J. Biotechnol., 2012, 158:1-7.

Dixon, "Natural products and plant disease resistance," Nature, 2001, 411:843-847.

Guiltinan, "Cacao: Biotechnology in Agriculture and Forestry—Transgenic crops VI," Pua and Davey (eds), Berlin Heidelberg: Springer Verlag, 2007, pp. 1-30.

Guiltinan et al. "Genomics of Theobroma cacao, 'The Food of the Gods,'—Genomics of tropical crop plants," Moore and Ming (eds), Berlin Heidelberg: Springer Verlag, 2008, pp. 145-171.

Howles et al. "Overexpression of L-phenylalanine ammonia-lyase in transgenic tobacco plants reveals control points for flux into phenylpropanoid biosynthesis," Plant Physiol., 1996, 112:1617-1624.

Jeong et al., "Differential expresion of kenaf phenylalanine ammonia-lyase (PAL) ortholog during developmental stages and in response to abiotic stresses," Plant Omics, 2012, vol. 5. [Retrieved from the Internet Dec. 13, 2013: <http://search.informit.com/au/documentSummary;dn=673347924562583;res=IELHSS>].

Lepelley et al., "Characterization, high-resolution mapping and differential expression of three homologous PAL genes in Coffea canephora Pierre (Rubiaceae)," Planta Epub, 2012, 236:313-326.

MacDonald et al., "A modern view of phenylalanine ammonia lyase," Biochem. Cell Biol., 2007, 85:273-282.

Mase et al., "The ectopic expression of phenylalanine ammonia lyase with ectopic accumulation of polysaccharide-linked hydroxycinnamoyl esters in internode parenchyma of rice mutant Fukei 71," Plant Cell Rep., 2005, 24:487-493.

NCBI Reference Sequence: NC_011770.1. Aeruginosa LESB58 chromosome, complete genome. Jun. 18, 2012.[Retrieved from the Internet Dec. 13, 2013: <http://www.ncbi.nlm.nih.gov/nuccore/218888746?sat=17&satkey=9409188>]; locus_tag="PLES-54831".

Ohl et al. "Functional properties of a phenylalanine ammonia-lyase promoter from Arabidopsis," Plant Cell, 1990, 2:837-848.

Okey et al. "Phytophthora canker resistance in Cacao: Role of peroxidase, polyphenoloxidase and phenylalanine ammonia-lyase," J. Phytopathol., 1997, 145:295-299.

Selleck et al. "Recombinant protein complex expression in *E. coli*," Curr. Protocols Protein Sci., 2008, Chapter 5, pp. 1-25.

Shadle et al. "Phenylpropanoid compounds and disease resistance in transgenic tobacco with altered expression of L-phenylalanine ammonia-lyase," Phytochem., 2003, 64:153-161.

International Search Report for PCT/US2013/052174 dated Aug. 18, 2014.

International Search Report for PCT/US2013/052245 dated Dec. 6, 2014.

Pirttila et al., "Chitinase production in pine callus (*Pinus sylvestris*L): a defense reaction against endophytes?" Planta, 2002, 214:848-852.

Rea et al., "Integrated plant biotechnologies applied to safer and healthier food production: the Nutra-Snack manufacturing chain," Food Sci. & Tech., 2011, 22:353-366.

Yang et al., "Tissue culture-based selection of high rosmarinic acid producing clones of Rosemary (*Rosmarinus officinalis* L.) using Pseudomonas Strain F," Food Biotech., 1997, 11:73-88.

Mewis et al "Specfic poly-phenolic compounds in cell culture of *Vtis vinifera* L. cv Gamay Freaux" Appl. Biochem, Biotechnol., 2011, 164:148-161.

Melnick et al., "Isolation of endophytic endospore-forming bacteria from Theobroma cacao as potential biological control agents of cacao diseases," Biol. Control, 2011, 57:236-245.

Flores-Sanchez et al., "Elicitation studies in cell suspension cultures of *Cannabis sativa* L., "J. Biotech., 2009, 143:157-168.

Al-Amier et al., "Tissue culture based screening for selection of high biomass and phenolic producing clonal lines of lavender using Pseudomonas and azetidine-2-carboxylate," J. Agric. Food Chem., 1999, 47:2937-2943.

Extended European Search Report for Application 13822321.9 dated Feb. 25, 2016.

* cited by examiner

METHODS FOR INCREASING THE PRODUCTION OF PHENOLIC COMPOUNDS FROM *THEOBROMA CACAO*

CROSS-REFERENCE TO RELATED APPLICATIONS

This application claims the priority benefit of U.S. Provisional Patent Application No. 61/675,869 filed Jul. 26, 2012, which are hereby incorporated herein by reference in their entireties.

CROSS REFERENCE TO SEQUENCE LISTING

The genetic components described herein are referred to by a sequence identifier number (SEQ ID NO). The SEQ ID NO corresponds numerically to the sequence identifiers <400>1, <400>2, etc. The Sequence Listing, in written computer readable format (CFR), is incorporated by reference in its entirety.

BACKGROUND

Tissue culturing is used in the propagation of new plant varieties, the production of doubled haploids, cryopreservation, conservation of rare and endangered plants, cultivation of difficult-to-propagate plants, and the production of secondary metabolites and transgenic plants. Tissue culturing focuses on the production of high quality, disease-free plant materials for the growth of crop plants and fruit trees. However, major challenges are still associated with the production and distribution of high quality plant materials for plant breeding and the rapid production of improved plants. Currently, tissue culturing is being used particularly for large-scale plant multiplication and micro-propagation, techniques which have wide applications in forestry and agriculture. Hundreds of commercial micro-propagation laboratories worldwide are currently multiplying large number of clones of desired varieties and local flora (IAEA, 2004).

Different opinions among members of the general public have been established regarding plant transformation, particularly by those highly concerned about environmental issues. By contrast, scientists recognize the plant that results from a specific targeted genetic alteration is indistinguishable from the plant that has been developed by a process of breeding and selection. The only difference is that the process of altering a target plant can be greatly accelerated because the genetic modifications can be directed rather than random. Directed modification by homologous recombination has been tested with homologous-recombination dependent gene targeting (hrdGT) (Doetschman et al., 1987) (Gupta & Dhugga, 2010). The problem with this approach is that the relative rate of homologous recombination compared to the rate of random insertion by illegitimate recombination is lower in plant cells than it is in animal cells. Efforts to address this limitation by the expression of foreign genes in plant cells have been made. These methods have had limited success in producing effective gene targeting. Moreover, even when these modified cells are used to effect homologous recombination, the resultant modified cell would still contain an exogenous gene used to select the homologous recombinants and thus still be considered a genetically modified plant by regulators and environmentally concerned entities.

Other methods in which homologous recombination is not involved and the utilization of specific recombination sites and recombinases derived from transposons have also been described in WO 01/85969 and WO 99/25821. The problem with this approach is the mixed structure of the oligonucleotide would likely prevent true recombination by genomic integration.

One of the most common techniques to genetically hybridize plants is the use of plasmid-carrying *Agrobacterium tumefaciens*. A part of the life cycle of the *A. tumefaciens* plasmid involves infection of plants. *A. tumefaciens* introduces the plasmid into the nuclei of plant cells in the form of single strands. A recombinant *A. tumefaciens* plasmid can be used to introduce exogenous DNA into a plant cell.

Different bacterial plasmid gene treatments have also been used. For example, a simple DNA recombinant plasmid or plasmid holding specific gene cassettes to ensure homologous recombination has been used. Plants hybridized by this method would be classified as genetically-modified organisms (GMOs) and would still be a problem for the food and pharmaceutical industries.

Methods for increasing the transgenic plant size and yield as well as delaying flowering in the plants, using nucleic acids that encode plant transcription factors, have been established (U.S. Pat. No. 7,858,848). However, these methods also involve genetically transforming the plants. Moreover, the extraction of secondary metabolites usually requires high initial amounts of plant biomass or material. In general, the extraction of plant metabolites is carried out from large amounts of fresh biomass material, which requires agronomic practices, the use of chemicals, and time consuming and expensive extraction methods.

SUMMARY

Described herein are methods for enhancing the production of phenolic compounds from *Theobroma cacao*. For example, the devices and methods described herein increase the production of phenolic compounds from cocoa plants, which has industrial and economic value. The phenolic compounds produced by the devices and methods do not require the ultra purification that is common in conventional or commercial methods. The devices and methods described herein also enhance the growth rate of plants.

The advantages of the invention will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below.

DETAILED DESCRIPTION

Figure 1:
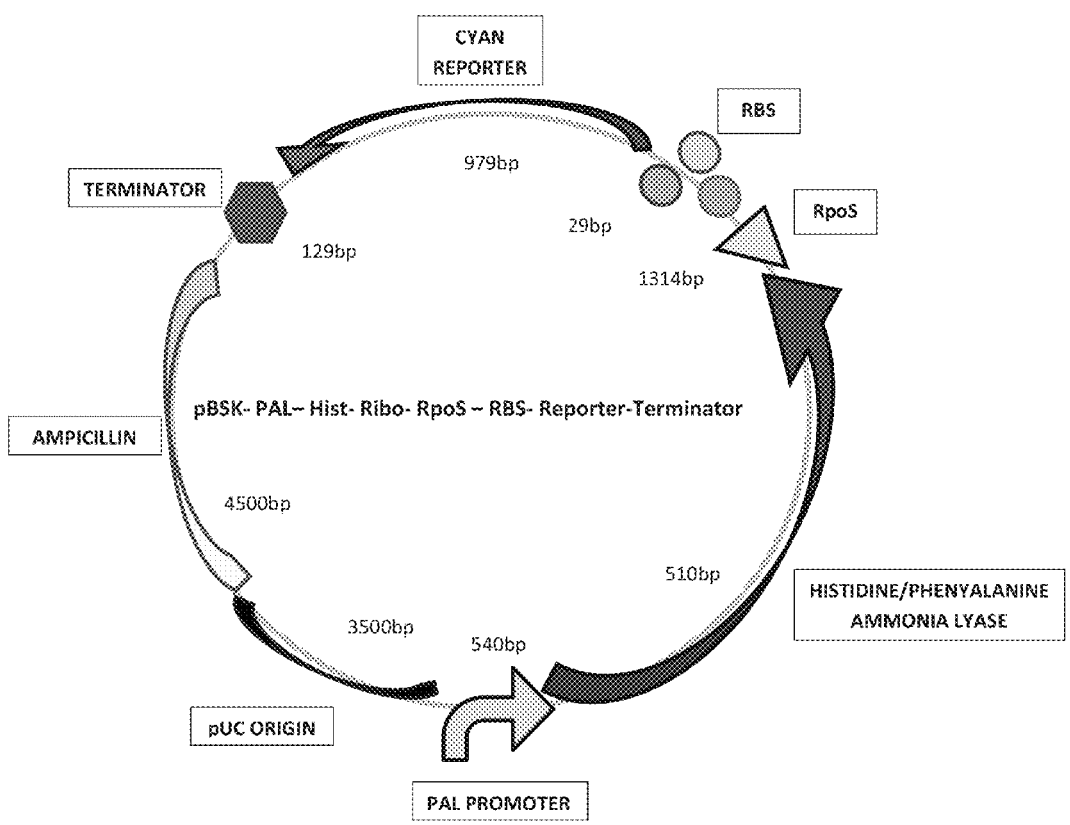
FIG. 1 shows a DNA construct described herein incorporated in a plasmid.
Figure 2:
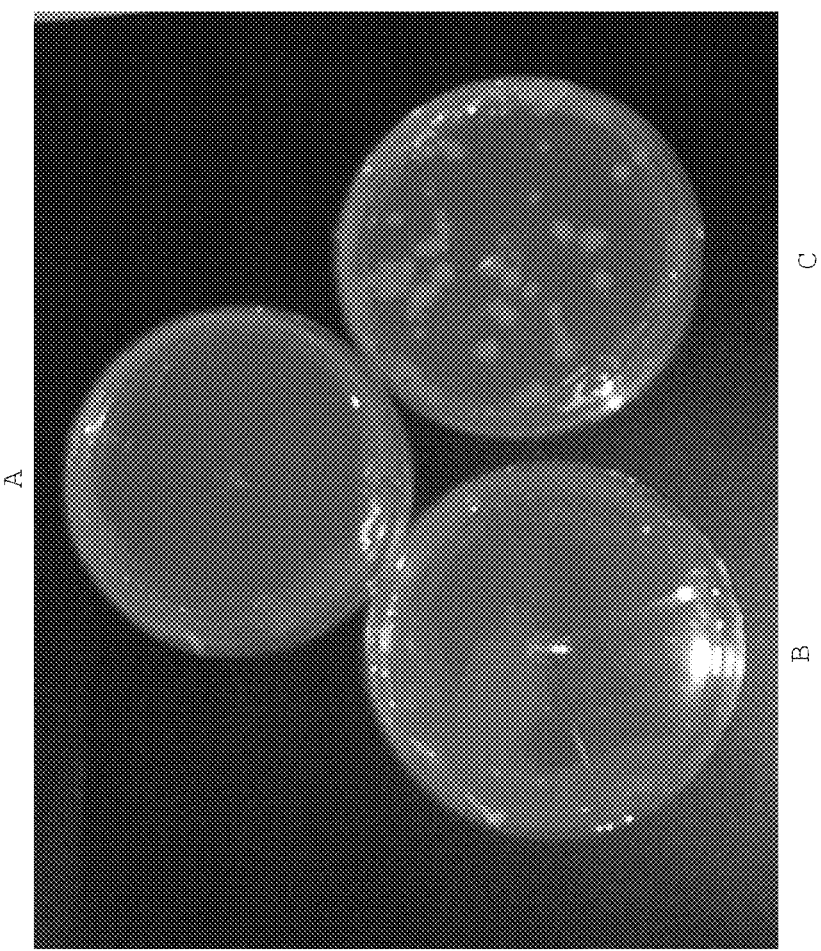
FIG. 2 shows colonies of *B. pumilus* device and control (*B. pumilus* without phenolic DNA). Colonies incorporating the *B. pumilus* device (bottom row) show higher colony populations than the control (top). Colonies in the bottom right Petri dish are the *B. pumilus* device containing the protein phenylalanine-ammonia lyase (PAL), which showed higher bacterial population.

Before the present compounds, compositions, articles, devices, and/or methods are disclosed and described, it is to be understood that the aspects described below are not limited to specific compounds, synthetic methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a," "an" and "the" include plural referents unless the context clearly dictates otherwise. Thus, for example, reference to "a bioactive agent" includes mixtures of two or more such agents, and the like.

"Optional" or "optionally" means that the subsequently described event or circumstance can or cannot occur, and that the description includes instances where the event or circumstance occurs and instances where it does not. For example, the phrase "optional ingredient" means that the ingredient may or may not be present.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

Disclosed are materials and components that can be used for, can be used in conjunction with, can be used in preparation for, or are products of the disclosed compositions and methods. These and other materials are disclosed herein, and it is understood that when combinations, subsets, interactions, groups, etc. of these materials are disclosed that while specific reference of each various individual and collective combination and permutation of these compounds may not be explicitly disclosed, each is specifically contemplated and described herein. For example, if a bacterium is disclosed and discussed and a number of different compatible bacterial plasmids are discussed, each and every combination and permutation of bacterium and bacterial plasmid that is possible is specifically contemplated unless specifically indicated to the contrary. For example, if a class of molecules A, B, and C are disclosed as well as a class of molecules D, E, and F, and an example of a combination molecule, A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E is specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, If a variety of additional steps can be performed, it is understood that each of these additional steps can be performed with any specific embodiment or combination of embodiments of the disclosed methods, and that each such combination is specifically contemplated and should be considered disclosed.

References in the specification and concluding claims to parts by weight, of a particular element or component in a composition or article, denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

Described herein are methods for enhancing the physiological of *Theobroma cacao*, which is also referred to herein as cocoa. The term "physiological property" as defined herein includes any physical, chemical, biochemical, or biological feature that is improved using the methods described herein. In one aspect, the methods can enhance the production of phenolic compounds produced by *Theobroma cacao*. In other aspects, the methods can enhance the growth rate of *Theobroma cacao*.

I. DNA Constructs and Biological Devices

As used herein, "plant" is used in a broad sense to include, for example, any species of woody, ornamental, crop, cereal, fruit, or vegetable plant, as well as photosynthetic green algae. "Plant" also refers to a plurality of plant cells that are differentiated into a structure that is present at any stage of a plant's development. Such structures include, but are not limited to, fruits, shoots, stems, leaves, flower petals, roots, tubers, corms, bulbs, seeds, gametes, cotyledons, hypocotyls, radicles, embryos, gametophytes, tumors, and the like. "Plant cell," "plant cells," or "plant tissue" as used herein refers to differentiated and undifferentiated tissues of plants including those present in any of the tissues described above, as well as to cells in culture such as, for example, single cells, protoplasts, embryos, calluses, etc.

"Heterologous" genes and proteins are genes and proteins that have been experimentally put into a cell that are not normally expressed by that cell. A heterologous gene may be cloned or derived from a different cell type or species than the recipient cell or organism. Heterologous genes may be introduced into cells by transduction or transformation.

An "isolated" nucleic acid is one that has been separated from other nucleic acid molecules and/or cellular material (peptides, proteins, lipids, saccharides, and the like) normally present in the natural source of the nucleic acid. An "isolated" nucleic acid may optionally be free of the flanking sequences found on either side of the nucleic acid as it naturally occurs. An isolated nucleic acid can be naturally occurring, can be chemically synthesized, or can be a cDNA molecule (i.e., is synthesized from an mRNA template using reverse transcriptase and DNA polymerase enzymes).

"Transformation" or "transfection" as used herein refers to a process for introducing heterologous DNA into a host cell. Transformation can occur under natural conditions or may be induced using various methods known in the art. Many methods for transformation are known in the art and the skilled practitioner will know how to choose the best transformation method based on the type of cells being transformed. Methods for transformation include, for example, viral infection, electroporation, lipofection, chemical transformation, and particle bombardment. Cells may be stably transformed (i.e., the heterologous DNA is capable of replicating as an autonomous plasmid or as part of the host chromosome) or may be transiently transformed (i.e., the heterologous DNA is expressed only for a limited period of time).

"Competent cells" refers to microbial cells capable of taking up heterologous DNA. Competent cells can be purchased from a commercial source, or cells may be made competent using procedures known in the art. Exemplary procedures for producing competent cells are provided in the Examples.

The biological devices described herein can be used to enhance the physiological properties of *Theobroma cacao*. In one aspect, the biological device can increase the production of phenolic compounds by *Theobroma cacao*. The device is generally composed of host cells, where the host cells are transformed with a DNA construct described herein that promotes the production of phenolic compounds in *Theobroma cacao*.

It is understood that one way to define the variants and derivatives of the genetic components and DNA constructs described herein is through defining the variants and derivatives in terms of homology/identity to specific known sequences. Those of skill in the art readily understand how to determine the homology of two nucleic acids. For example, the homology can be calculated after aligning the two sequences so that the homology is at its highest level. Another way of calculating homology can be performed by published algorithms (see Zuker, M. *Science* 244:48-52, 1989, Jaeger et al. *Proc. Natl. Acad. Sci. USA* 86:7706-7710, 1989, Jaeger et al. *Methods Enzymol.* 183:281-306, 1989, which are herein incorporated by reference for at least material related to nucleic acid alignment).

As used herein, "conservative" mutations are mutations that result in an amino acid change in the protein produced from a sequence of DNA. When a conservative mutation occurs, the new amino acid has similar properties as the wild type amino acid and generally does not drastically change the function or folding of the protein (e.g., switching isoleucine for valine is a conservative mutation since both are small, branched, hydrophobic amino acids). "Silent mutations," meanwhile, change the nucleic acid sequence of a gene encoding a protein but do not change the amino acid sequence of the protein.

It is understood that the description of conservative mutations and homology can be combined together in any combination, such as embodiments that have at least 70%, 75%, 80%, 85%, 90%, 95%, or 99% homology to a particular sequence wherein the variants are conservative mutations. It is understood that any of the sequences described herein can be a variant or derivative having the homology values listed above.

In one aspect, the DNA construct described herein (referred to herein as "phenolic DNA") can promote the expression of one or more phenolic compounds from *Theobroma cacao*. The term "phenolic compound" is defined as any aromatic compound having at least one hydroxyl group present on an aromatic ring. Examples of such phenolic compounds include, but are not to, gallic acid, p-hydroxybenzoic acid, caffeic acid, catechin, and p-coumaric acid.

In one aspect, the DNA construct is from 5' to 3' the genetic components in the following order: (1) a PAL promoter, (2) a gene that expresses histidine/phenylalanine ammonia-lyase, (3) a ribosomal binding site, and (4) a terminator. In certain aspects, the DNA construct further comprises a ribosomal switch between the gene that expresses histidine/phenylalanine ammonia-lyase and the ribosomal binding site that can enhance translation and protein expression.

In one aspect, the gene that expresses histidine/phenylalanine ammonia lyase is isolated from bacteria. In one aspect, the bacteria are *Pseudomonas* species. In a further aspect, the bacteria are *P. aeruginosa, P. dentrificans, P. resinovorans, P. protegens, P. fluorescens*, or another *Pseudomonas* species. In another aspect, the gene that expresses histidine/phenylalanine ammonia lyase is isolated from plants. In one aspect, the plants are *Arabidopsis thaliana*. In another aspect, the plants are *Selaginella moellendorffii, Physcomitrella patens*, corn (*Zea mays*), or sorghum or milo (*Sorghum bicolor*). In a further aspect, the gene that expresses phenylalanine ammonia lyase in the DNA construct has SEQ ID NO. 5 or a derivative or variant thereof. In another aspect, the gene that expresses phenylalanine ammonia lyase in the DNA construct has SEQ ID NOS. 6 or 7 or a derivative or variant thereof.

In another aspect, the DNA construct further includes (5) a gene that confers resistance to an antibiotic (a "selective marker"), (6) a reporter protein, or a combination thereof.

In one aspect, a regulatory sequence is already incorporated into a vector such as, for example, a plasmid, prior to genetic manipulation of the vector. In another aspect, the regulatory sequence can be incorporated into the vector through the use of restriction enzymes or any other technique known in the art.

In one aspect, the regulatory sequence is a promoter. The term "promoter" refers to a DNA sequence capable of controlling the expression of a coding sequence. In one aspect, the coding sequence to be controlled is located 3' to the promoter. In another aspect, the promoter is derived from a native gene. In an alternative aspect, the promoter is composed of multiple elements derived from different genes and/or promoters. A promoter can be assembled from elements found in nature, from artificial and/or synthetic elements, or from a combination thereof. It is understood by those skilled in the art that different promoters can direct the expression of a gene in different tissues or cell types, at different stages of development, in response to different environmental or physiological conditions, and/or in different species. In one aspect, the promoter functions as a switch to activate the expression of a gene.

In one aspect, the promoter is "constitutive." A constitutive promoter is a promoter that causes a gene to be expressed in most cell types at most times. In another aspect, the promoter is "regulated." A regulated promoter is a promoter that becomes active in response to a specific stimulus. A promoter may be regulated chemically, such as, for example, in response to the presence or absence of a particular metabolite (e.g., lactose or tryptophan), a metal ion, a molecule secreted by a pathogen, or the like. A promoter may also be regulated physically, such as, for example, in response to heat, cold, water stress, salt stress, oxygen concentration, illumination, wounding, or the like.

Promoters that are useful to drive expression of the nucleotide sequences described herein are numerous and familiar to those skilled in the art. Suitable promoters include, but are not limited to, the following: PAL promoter, T3 promoter, T7 promoter, Fe promoter, and GAL1 promoter. Variants of these promoters are also contemplated. The skilled artisan will be able to use site-directed mutagenesis and/or other mutagenesis techniques to modify the promoters to promote more efficient function. The promoter may be positioned, for example, from 10-100 nucleotides away from a ribosomal binding site.

In one aspect, the promoter is a PAL promoter. In one aspect, the PAL promoter in the DNA construct is SEQ ID NO. 1 or a derivative or variant thereof. In another aspect, the PAL promoter is SEQ ID NOS. 2, 3, or 4 or a derivative or variant thereof.

In another aspect, the gene that expresses histidine/phenylalanine ammonia-lyase in the DNA construct is SEQ ID NO. 5 or a derivative or variant thereof. In another aspect, the gene is SEQ ID NOS. 6 or 7 or a derivative or variant thereof.

The selection of the ribosomal binding site (and optional) ribosomal switch can vary depending upon the selection of the host cells. In one aspect, the ribosomal binding site in the DNA construct is SEQ ID NOS. 8 or 9, or a derivative or variant thereof (e.g., where n in SEQ ID NO. 8 can be A, T, G, or C). In certain aspects, when the DNA construct further includes a ribosomal switch. In one aspect, the ribosomal switch is SEQ ID NOS. 11, 12, 13 or 14, or a derivative or variant thereof.

In another aspect, the regulatory sequence is a terminator or stop sequence. As used herein, a terminator is a sequence of DNA that marks the end of a gene or operon to be transcribed. In a further aspect, the terminator is an intrinsic terminator or a Rho-dependent transcription terminator. As used herein, an "intrinsic terminator" is a sequence wherein a hairpin structure can form in the nascent transcript and wherein the hairpin disrupts the mRNA/DNA/RNA polymerase complex. As used herein, a "Rho-dependent" transcription terminator requires a Rho factor protein complex to disrupt the mRNA/DNA/RNA polymerase complex.

In another aspect, the terminator in the DNA construct is SEQ ID NO. 10 or a derivative or variant thereof.

In a further aspect, the regulatory sequence includes both a promoter and a terminator or stop sequence. In a still further aspect, the regulatory sequence can include multiple promoters or terminators. Other regulatory elements, such as enhancers, are also contemplated. Enhancers may be located from about 1 to about 2000 nucleotides in the 5' direction from the start codon of the DNA to be transcribed, or may be located 3' to the DNA to be transcribed. Enhancers may be "cis-acting," that is, located on the same molecule of DNA as the gene whose expression they affect.

In certain aspects, the DNA construct can include a gene that expresses a reporter protein. The selection of the reporter protein can vary. For example, the reporter protein can be a yellow fluorescent protein, red fluorescent protein, a green fluorescent protein, or a cyan fluorescent protein. In one aspect, the gene that expresses the reporter protein has SEQ ID NO. 15. The amount of fluorescence that is produced by the biological device can be correlated to the amount of DNA construct incorporated into the plant cells. The fluorescence produced by the device can be detected and quantified using techniques known in the art. For example, spectrofluorometers are typically used to measure fluorescence. The Examples provide exemplary procedures for measuring the amount of fluorescence as a result of the expression of DNA.

The DNA construct described herein can be part of a vector. In one aspect, the vector is a plasmid, a phagemid, a cosmid, a yeast artificial chromosome, a bacterial artificial chromosome, a virus, a phage, or a transposon.

In general, plasmid vectors containing replicon and control sequences that are derived from species compatible with the host cell are used in connection with these hosts. Vectors capable of high levels of expression of recombinant genes and proteins are well known in the art. The vector ordinarily carries a replication origin as well as marking sequences that are capable of providing phenotypic selection in transformed cells. Plasmid vectors useful for the transformation of a variety of host cells are well known and are commercially available. Such vectors include, but are not limited to, pWLNEO, pSV2CAT, pOG44, PXT1, pSG (Stratagene), pSVK3, pBSK, pBR322, pYES, pYES2, pBSKII, and pUC vectors.

Plasmids are double-stranded, autonomously-replicating, genetic elements that are not integrated into host cell chromosomes. Further, these genetic elements are usually not part of the host cell's central metabolism. In bacteria, plasmids may range from 1 kilobase (kb) to over 200 kb. Plasmids can be engineered to encode a number of useful traits including the production of secondary metabolites, antibiotic resistance, the production of useful proteins, degradation of complex molecules and/or environmental toxins, and others. Plasmids have been the subject of much research in the field of genetic engineering, as plasmids are convenient expression vectors for foreign DNA in, for example, microorganisms. Plasmids generally contain regulatory elements such as promoters and terminators and also usually have independent replication origins. Ideally, plasmids will be present in multiple copies per host cell and will contain selectable markers (such as genes for antibiotic resistance) to allow the ordinarily skilled artisan to select host cells that have been successfully transfected with the plasmids (for example, by culturing the host cells in a medium containing the antibiotic).

In one aspect, the vector encodes a selection marker. In a further aspect, the selection marker is a gene that confers resistance to an antibiotic. In certain aspects, during fermentation of host cells transformed with the vector, the cells are contacted with the antibiotic. For example, the antibiotic may be included in the culture medium. Cells that have not been successfully transformed cannot survive in the presence of the antibiotic; only cells containing the vector that confers antibiotic resistance can survive. Optionally, only cells containing the vector to be expressed will be cultured, as this will result in the highest production efficiency of the desired gene products (e.g., peptides involved in the synthesis of phenolic compounds). Cells that do not contain the vector would otherwise compete with transformed cells for resources. In one aspect, the antibiotic is tetracycline, neomycin, kanamycin, ampicillin, hygromycin, chloramphenicol, amphotericin B, bacitracin, carbapenam, cephalosporin, ethambutol, fluoroquinolones, isonizid, methicillin, oxacillin, vancomycin, streptomycin, quinolines, rifampin, rifampicin, sulfonamides, cephalothin, erythromycin, streptomycin, gentamycin, penicillin, other commonly-used antibiotics, or a combination thereof.

In one aspect, when the vector is a plasmid, the plasmid can also contain a multiple cloning site or polylinker. In a further aspect, the polylinker contains recognition sites for multiple restriction enzymes. The polylinker can contain up to 2, 3, 4, 5, 6, 7, 8, 9, 10, 11, 12, 13, 14, 15, 16, 17, 18, 19, 20, or more than 20 recognition sites for restriction enzymes. Further, restriction sites may be added, disabled, or removed as required, using techniques known in the art. In one aspect, the plasmid contains restriction sites for any known restriction enzyme such as, for example, HindIII, KpnI, SacI, BamHI, BstXI, EcoRI, BsaBI, NotI, XhoI, SphI, SbaI, ApaI, SalI, ClaI, EcoRV, PstI, SmaI, XmaI, SpeI, EagI, SacII, or any combination thereof. In a further aspect, the plasmid contains more than one recognition site for the same restriction enzyme.

In one aspect, the restriction enzyme can cleave DNA at a palindromic or an asymmetrical restriction site. In a further aspect, the restriction enzyme cleaves DNA to leave blunt ends; in an alternative aspect, the restriction enzyme cleaves DNA to leave "sticky" or overhanging ends. In another aspect, the enzyme can cleave DNA a distance of from 20 bases to over 1000 bases away from the restriction site. A variety of restriction enzymes are commercially available and their recognition sequences, as well as instructions for use (e.g. amount of DNA needed, precise volumes of reagents, purification techniques, as well as information about salt concentration, pH, optimum temperature, incubation time, and the like) are made available by commercial enzyme suppliers.

In one aspect, a plasmid with a polylinker containing one or more restriction sites can be digested with one restriction enzyme and a nucleotide sequence of interest can be ligated into the plasmid using a commercially-available DNA ligase enzyme. Several such enzymes are available, often as kits containing all reagents and instructions required for use. In another aspect, a plasmid with a polylinker containing two or more restriction sites can be simultaneously digested with two restriction enzymes and a nucleotide sequence of interest can be ligated into the plasmid using a DNA ligase enzyme. Using two restriction enzymes provides an asymmetric cut in the DNA, allowing for insertion of a nucleotide sequence of interest in a particular direction and/or on a particular strand of the double-stranded plasmid. Since RNA synthesis from a DNA template proceeds from 5' to 3', often starting just after a promoter, the order and direction of elements inserted into a plasmid is especially important. If a plasmid is to be simultaneously digested with multiple restriction enzymes, these enzymes must be compatible in terms of buffer, salt concentration, and other incubation parameters.

In some aspects, prior to ligation using a ligase enzyme, a plasmid that has been digested with a restriction enzyme is treated with an alkaline phosphatase enzyme to remove 5' terminal phosphate groups. This prevents self-ligation of the plasmid and thus facilitates ligation of heterologous nucleic acid fragments into the plasmid.

In one aspect, the nucleic acids (e.g., genes that express histidine/phenylalanine ammonia lyase) used in the DNA constructs described herein can be amplified using the polymerase chain reaction (PCR) prior to being ligated into a plasmid or other vector. Typically, PCR-amplification techniques make use of primers or short, chemically-synthesized oligonucleotides that are complementary to regions on each respective strand flanking the DNA or nucleotide sequence to be amplified. A person having ordinary skill in the art will be able to design or choose primers based on the desired experimental conditions. In general, primers should be designed to provide for efficient and faithful replication of the target nucleic acids. Two primers are required for the amplification of each gene, one for the sense strand (that is, the strand containing the gene of interest) and one for the antisense strand (that is, the strand complementary to the gene of interest). Pairs of primers should have similar melting temperatures that are close to the PCR reaction's annealing temperature. In order to facilitate the PCR reaction, the following features should be avoided in primers: mononucleotide repeats, complementarity with other primers in the mixture, self-complementarity, and internal hairpins and/or loops. Methods of primer design are known in the art; additionally, computer programs exist that can assist the ordinarily skilled practitioner with primer design. Primers can optionally incorporate restriction enzyme recognition sites at their 5' ends to assist in later ligation into plasmids or other vectors.

PCR can be carried out using purified DNA, unpurified DNA that has been integrated into a vector, or unpurified genomic DNA. The process for amplifying target DNA using PCR consists of introducing an excess of two primers having the characteristics described above to a mixture containing the sequence to be amplified, followed by a series of thermal cycles in the presence of a heat-tolerant or thermophilic DNA polymerase, such as, for example, any of Taq, Pfu, Pwo, Tfl, rTth, Tli, or Tma polymerases. A PCR "cycle" involves denaturation of the DNA through heating, followed by annealing of the primers to the target DNA, followed by extension of the primers using the thermophilic DNA polymerase and a supply of deoxynucleotide triphosphates (i.e., dCTP, dATP, dGTP, and TTP), along with buffers, salts, and other reagents as needed. In one aspect, the DNA segments created by primer extension during the PCR process can serve as templates for additional PCR cycles. Many PCR cycles can be performed to generate a large concentration of target DNA or gene. PCR can optionally be performed in a device or machine with programmable temperature cycles for denaturation, annealing, and extension steps. Further, PCR can be performed on multiple genes simultaneously in the same reaction vessel or microcentrifuge tube since the primers chosen will be specific to selected genes. PCR products can be purified by techniques known in the art such as, for example, gel electrophoresis followed by extraction from the gel using commercial kits and reagents.

In a further aspect, the vector can include an origin of replication, allowing it to use the host cell's replication machinery to create copies of itself.

As used herein, "operably linked" refers to the association of nucleic acid sequences on a single nucleic acid fragment so that the function of one affects the function of another. For example, if sequences for multiple genes are inserted into a single plasmid, their expression may be operably linked. Alternatively, a promoter is said to be operably linked with a coding sequence when it is capable of affecting the expression of the coding sequence.

As used herein, "expression" refers to transcription and/or accumulation of an mRNA derived from a gene or DNA fragment. Expression may also be used to refer to translation of mRNA into a peptide, polypeptide, or protein.

Exemplary methods for producing the DNA constructs described herein are provided in the Examples. Restriction enzymes and purification techniques known in the art can be used to prepare the DNA constructs. After the vector incorporating the DNA construct has been produced, it can be incorporated into host cells using the methods described below.

II. Biological Devices

In one aspect, a "biological device" is formed when a microbial cell is transfected with the DNA construct described herein. The biological devices are generally composed of microbial host cells, where the host cells are transformed with a DNA construct described herein.

In one aspect, the DNA construct is carried by the expression vector into the cell and is separate from the host cell's genome. In another aspect, the DNA construct is incorporated into the host cell's genome. In still another aspect, incorporation of the DNA construct into the host cell enables the host cell to produce phenolic compounds.

The host cells as referred to herein include their progeny, which are any and all subsequent generations formed by cell division. It is understood that all progeny may not be identical due to deliberate or inadvertent mutations. A host cell may be "transfected" or "transformed," which refers to a process by which exogenous nucleic acid is transferred or introduced into the host cell. A transformed cell includes the primary subject cell and its progeny. The host cells can be naturally occurring cells or "recombinant" cells. Recombinant cells are distinguishable from naturally occurring cells in that they do not contain nucleic acid sequences introduced using molecular biology techniques. In one aspect, host cells that naturally associate with *Theobroma cacao* can be used herein. In one aspect, the host cell is a prokaryotic cell, such as, for example, *Bacillus pumilus* or *E. coli*. In other aspects, the host cell is a yeast such as, for example, *Saccharomyces cerevisiae*. Host cells transformed with the DNA construct described herein are referred to as biological devices.

The DNA construct is first delivered into the host cell. This delivery may be accomplished in vitro, using well-developed laboratory procedures for transforming cells lines. Transformation of bacterial cell lines can be achieved using a variety of techniques. One method includes calcium chloride. The exposure to the calcium ions renders the cells able to take up the DNA construct. Another method is electroporation. In this technique, a high-voltage electric field is applied briefly to cells, producing transient holes in the cell membrane through which the vector containing the DNA construct enters. Exemplary procedures for transforming yeast and bacteria with specific DNA described herein are provided in the Examples. In certain aspects, two or more types of DNA can be incorporated into the host cells. Thus, different metabolites can be produced from the same plant at enhanced rates.

Once the DNA construct has been incorporated into the host cell, the cells are cultured such that the cells multiply. A satisfactory microbiological culture contains available sources of hydrogen donors and acceptors, carbon, nitrogen, sulfur, phosphorus, inorganic salts, and, in certain cases, vitamins or other growth promoting substances. The addition of peptone provides a readily available source of nitrogen and carbon. A variety of other carbon sources are contemplated, including, but not limited to: monosaccharides such as glucose and fructose, disaccharides such as lactose and sucrose, oligosaccharides, polysaccharides such as starch, and mixtures thereof. Unpurified mixtures extracted from feedstocks are also contemplated and can include molasses, barley malt, and related compounds and compositions. Other glycolytic and tricarboxylic acid cycle intermediates are also contemplated as carbon sources, as are one-carbon substrates such as carbon dioxide and/or methanol in the cases of compatible organisms. The carbon source utilized is limited only by the particular organism being cultured.

Furthermore, the use of different media results in different growth rates and different stationary phase densities. Secondary metabolite production is highest when cells are in stationary phase. A rich media results in a short doubling time and higher cell density at stationary phase. Minimal media results in slow growth and low final cell densities. Efficient agitation and aeration increase final cell densities. A skilled artisan will be able to determine which type of media is best suited to culture a particular species and/or strain of host cell.

Culturing or fermenting of host cells may be accomplished by any technique known in the art. In one aspect, batch fermentation can be conducted. In batch fermentation, the composition of the culture medium is set at the beginning of culturing and the system is closed to future artificial alterations. In some aspects, a limited form of batch fermentation can be carried out, wherein factors such as oxygen concentration and pH are manipulated, but additional carbon is not added. Continuous fermentation methods are also contemplated. In continuous fermentation, equal amounts of a defined medium are continuously added to and removed from a bioreactor. In other aspects, microbial host cells are immobilized on a substrate. Fermentation can be carried out on any scale and may include methods in which literal "fermentation" is carried out as well as other culture methods that are non-fermentative.

III. Methods for Enhancing the Physiological Properties of *Theobroma cacao*,

In one aspect, when *Theobroma cacao* calluses are contacted with the biological devices described above, the production of phenolic compounds is enhanced. Exemplary procedures for growing *Theobroma cacao* calluses are provided in the Examples. In one aspect, *Theobroma cacao* calluses grown from 2 to 6 weeks, from 3 to 6 weeks, from 4 to 6 weeks, or for about 5 weeks can be used herein.

In one aspect, plant cells when contacted with the biological devices described above exhibit enhanced production of phenolic compounds. Recipient cell targets include, but are not limited to, meristem cells, Type I, Type II, and Type III callus, immature embryos and gametic cells such as microspores, pollen, sperm, and egg cells. It is contemplated that any cell from which a fertile plant may be regenerated is useful as a recipient cell. Type I, Type II, and Type III callus may be initiated from tissue sources including, but not limited to, immature embryos, immature inflorescences, seedling apical meristems, microspores, and the like. Those cells that are capable of proliferating as callus also are also useful herein. Methods for growing plant cells are known in the art (see U.S. Pat. No. 7,919,679). Exemplary procedures for growing plant calluses are provided in the Examples. In one aspect, plant calluses grown from 2 to 4 weeks can be used herein. The plant cells can also be derived from plants varying in age. For example, plants that are 80 days to 120 days old after pollination can be used to produce calluses useful herein.

The *Theobroma cacao* calluses can be contacted with the biological device in a number of different ways. In one aspect, the device can be added to a media containing the *Theobroma cacao* callus. In another aspect, the device can be injected into the *Theobroma cacao* callus via syringe. The amount of device and the duration of exposure to the device can vary as well. In one aspect, the concentration of the device is about $10^3$, $10^4$, $10^5$, $10^6$, $10^7$, $10^8$, or $10^9$ cells/mL of water. In one aspect, when the host cell is bacteria the concentration of the device is $10^6$. In another aspect, when the host cell is yeast, the concentration of the device is $10^9$. Different volumes of the biological device can be used as well, ranging from 25 µL to 500 µL.

Once the *Theobroma cacao* callus has been in contact with the biological device for a sufficient time to produce phenolic compounds, the phenolic compounds are isolated. In one aspect, the phenolic compounds are extracted from the media containing the biological device and the *Theobroma cacao* callus. The selection of the extraction solvent can vary depending upon the solubility of the metabolite. Exemplary procedures for extracting metabolites produced by the biological devices described herein are provided in the Examples.

With current techniques, the extraction of metabolites produced from plants usually requires high amounts of initial plant biomass or material, which in turn requires larger amounts of extraction solvents. The use of higher amounts of extraction solvents adds to the expense of producing phenolic compounds. The use of higher amounts of organic solvents presents environmental risks, as well. However, the use of the biological devices described herein produce significantly higher amounts of metabolite such as phenolic compounds from *Theobroma cacao*, which means smaller amounts of biomass are required in order to produce and isolate the metabolites when compared with existing techniques. Additionally, as will be shown below in the Examples, the biological devices described herein produce a number of different phenolic compounds, which is also desirable. The extraction of plant metabolites using current techniques also requires fresh biomass, which entails agronomic practices, the use of chemicals, and time consuming extraction methods. Therefore, the use of the biological devices described herein is more cost-effective and safer for the environment than traditional methods for synthesizing and extracting phenolic compounds. In one aspect, the methods described herein enhance the production of one or more phenolic compounds from *Theobroma cacao*, shorten the time required for production of phenolic compounds, and overcome the problem of unpredictable production levels of phenolic compounds from naturally-grown *Theobroma cacao* due to harsh environmental conditions.

In other aspects, the devices and methods described herein can increase the growth rate of a *Theobroma cacao* plant. In particular, the devices and methods described herein are effective in accelerating *Theobroma cacao* plant development in the early stages of tissue culturing. By accelerating plant development in the early stages, it is possible to harvest more metabolites from the plant. Additionally, the devices and methods described herein protect plant tissue cultures against microbial contamination, which is a problem associated with tissue culturing. Finally, conventional methods for tissue culture involve the use of synthetic growth factors such as 2-4-D, which can pose environmental concerns. The devices and methods described herein avoid the need for such compounds.

In certain aspects, the biological devices described herein can be used in combination with a polysaccharide to enhance one or more physiological properties of the plant. In one aspect, *Theobroma cacao* cells are first contacted with the biological device, then subsequently contacted with the polysaccharide. In another aspect, the *Theobroma cacao* cells are first contacted with the polysaccharide, then subsequently contacted with the biological device. In a further aspect, the plant cells are only contacted with a polysaccharide and not contacted with the biological device. In a still further aspect, the plant cells are contacted simultaneously with the polysaccharide and the biological device.

In one aspect, the polysaccharide includes chitosan, glucosamine (GlcN), N-acetylglucosamine (NAG), or any combination thereof. Chitosan is generally composed of glucosamine units and N-acetylglucosamine units and can be chemically or enzymatically extracted from chitin, which is a component of arthropod exoskeletons and fungal and microbial cell walls. In certain aspects, the chitosan can be acetylated to a specific degree of acetylation in order to enhance tissue growth during culturing as well as metabolite production. In one aspect, the chitosan is from 60% to about 100%, 70% to 90%, 75% to 85%, or about 80% acetylated. Exemplary procedures for producing and isolating the chitosan are provided in the Examples. In one aspect, chitosan isolated from the shells of crab, shrimp, lobster, and/or krill is useful herein.

The molecular weight of the chitosan can vary, as well. For example, the chitosan comprises about 3, 4, 5, 6, 7, 8, 9, 10, 11, 12, 13, 14, 15, 16, 17, 18, 19, or 20 glucosamine units and/or N-acetylglucosamine units. In another aspect, the chitosan includes 5 to 7 glucosamine units and/or N-acetylglucosamine units. In one aspect, the chitosan is in a solution of water and acetic acid at less than 1% by weight, less than 0.75% by weight, less than 0.50% by weight, less than 0.25% by weight, or less than 0.10% by weight. In another aspect, amount of chitosan that is applied to the plant cells is from 0.10% to 0.01% by weight, from 0.075% to 0.025% by weight, or is about 0.05% by weight. The polysaccharides used herein are generally natural polymers and thus present no environmental concerns. Additionally, the polysaccharide can be used in acceptably low concentrations. In certain aspects, the polysaccharide can be used in combination with one or more growth regulators.

In one aspect, the plant growth regulator is an auxin, a cytokinin, a gibberellin, abscisic acid, or a polyamine. In a further aspect, the auxin is a natural or synthetic auxin. In a still further aspect, the auxin is indole-3-acetic acid (IAA), 4-chloroindole-3-acetic acid (4-Cl-IAA), 2-phenylacetic acid (PAA), indole-3-butyric acid (IBA), 2,4-dichlorophenoxyacetic acid (2,4-D), α-naphthalene acetic acid (α-NAA), 2-methoxy-3,6-dichlorobenzoic acid (dicamba), 4-amino-3,5,6-trichloropicolinic acid (torden or picloram), 2,4,5-trichloropicolinic acid (2,4,5-T), or a combination thereof. In another aspect, the cytokinin is zeatin, kinetin, 6-benzylaminopurine, diphenylurea, thidizuron (TDZ), 6-(γ, γ-dimethylallylamino)purine, or a combination thereof. In another aspect, the gibberellin is gibberellin A1 (GA1), gibberellic acid (GA3), ent-gibberellane, ent-kaurene, or a combination thereof. In yet another aspect, the polyamine is putrescine, spermidine, or a combination thereof.

In one aspect, the plant cell or callus is first contacted with a polysaccharide and subsequently contacted with a plant growth regulator. In another aspect, the plant cell or callus is first contacted with a plant growth regulator and subsequently contacted with a polysaccharide. In an alternative aspect, the plant cell or callus is simultaneously contacted with a polysaccharide and a plant growth regulator. In a further aspect, the plant cell or callus is only contacted with a polysaccharide and is not contacted with a plant growth regulator.

The *Theobroma cacao* cells can be contacted with the polysaccharide using a number of techniques. In one aspect, the plant cells or reproductive organs (e.g., a plant embryo) can be cultured in agar and medium with a solution of the polysaccharide. In other aspects, the polysaccharide can be applied to a *Theobroma cacao* callus by techniques such as, for example, coating the callus (e.g., by spraying or another method) or injecting the polysaccharide into the callus. The amount of polysaccharide can vary depending upon, amongst other things, the selection and number of plant cells. The use of the polysaccharide in the methods described herein permits rapid tissue culturing at room temperature. Due to the ability to prevent microbial contamination, the tissue cultures can grow for extended periods of time ranging from days to several weeks. Moreover, tissue culturing with the polysaccharide can occur in the dark and/or light.

As discussed above, the plant cells can optionally be contacted with any of the biological devices described herein. Thus, the use of the polysaccharides and biological devices described herein is a versatile way to culture and grow *Theobroma cacao* cells with enhanced physiological properties.

In other aspects, the *Theobroma cacao* cells can be cultured in a liquid medium on a larger scale in a bioreactor. For example, *Theobroma cacao* cells can be cultured in agar and medium, then subsequently contacted with (e.g., injected) with a biological device described herein. After a sufficient culturing time (e.g., two to four weeks), the *Theobroma cacao* cells are introduced into a container with the same medium used above and the polysaccharide. In certain aspects, the polysaccharide can be introduced with anionic polysaccharides including, but not limited to alginates (e.g., sodium, calcium, potassium, etc.). After the introduction of the polysaccharide, the solution is mixed for a sufficient time to produce a desired result (e.g., production of a desired metabolite).

In one aspect, the plant callus is immersed in a solution of polysaccharide (e.g., chitosan) then inoculated with device. In one aspect, the plant callus is that of cocoa (*Theobroma cacao*). The plant callus can be from 2 days up to 20 days old prior to inoculation with the device. The plant callus is then allowed to grow until it is of sufficient weight and size. In one aspect, the plant callus is allowed to grow (i.e., culture) for 1 to 10 weeks after inoculation. The next step involves removal of the phenolic compounds from the callus. In one aspect, the callus is macerated with a solvent to produce a macerate. The macerate is then extracted with a solvent to in order to remove phenolic compounds. The extraction solvent is not a harsh solvent, and is generally environmentally friendly. In one aspect, the extraction solvent is acetone. Exemplary methods for producing calluses using the devices described herein and extractions of phenolic compounds are provided in the Examples.

In one aspect, phenolic compounds produced from a plant callus can be useful in pharmaceutical applications. Not wishing to be bound by theory, the phenolic compounds produced from callus will have fewer impurities and thus will be easier to purify for pharmaceutical applications.

In another aspect, a plant callus described above can be planted and allowed to grow and mature into a plant bearing fruit and leaves. In one aspect, phenolic compounds can be isolated from a plant that has been grown from a plant callus inoculated with a device described herein and optionally contacted with a polysaccharide (e.g., chitosan). In one aspect, phenolic compounds can be removed from fruit, seeds, or leaves of a plant grown with the devices described herein. In one aspect, the fruit and leaves of *Theobroma cacao* grown from calluses inoculated with the devices described herein provide a rich source of phenolic compounds. Exemplary methods for isolating phenolic compounds from the fruit and seeds of *Theobroma cacao* are provided in the Examples.

In one aspect, the fruits, seeds, and leaves of plants grown with the assistance of the devices described herein can be useful in the production of a number of food products where the food product is enriched with phenolic compounds. The consumer would then be eating natural products with increased levels of phenolic compounds, which provide health benefits.

In one aspect, the amount of phenolic compounds produced by the plant cells, plant callus, and/or plants that have been contacted with the biological device as described herein is from 1.1 to 4-fold greater than the amount of phenolic compounds produced by otherwise identical plant cells, plant callus, and/or plants that have not been contacted with the biological device as described herein.

The devices and methods described herein also enhance the growth rate of plants. For example, plants grown using the devices and methods described herein can be grown in 2 to 4 weeks versus the 32 weeks typically required for conventional field growth. Therefore, more plants can be harvested and, thus, more phenolic compounds can be produced and isolated in a shorter period of time. Moreover, the devices and methods described herein do not require the use of synthetic chemicals and can be used in a closed environment and not in the field. Thus, the devices and methods described herein provide a versatile and cost-effective way to grow plants and produce desirable metabolites in significant quantities.

The devices and methods described herein also enhance the growth rate of *Theobroma cacao*. For example, *Theobroma cacao* grown using the devices and methods described herein can be grown in 2 to 4 weeks versus 32 months typically required for conventional field growth. Moreover, the devices and methods described herein do not require the use of synthetic chemicals and can be used in a closed environment and not in the field. Thus, the devices and methods described herein provide a versatile and cost-effective way to grow plants and produce desirable metabolites in significant quantities.

In another embodiment, the metabolite produced by the devices and methods described herein can be used to prevent the *Theobroma cacao* from contracting one or more diseases and enhance the physical properties of the plant. For example, the metabolites can be used as antifungal agents.

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions Preparation of DNA Construct The DNA construct was composed of genetic components described herein and assembled in plasmid vectors (e.g., pYES and pBSKII). Experimental laboratory procedures were followed (Gietz, R. D. and R. H. Schiestl, 2007, *Nature Protocols*, "Quick and easy yeast transformation using the LiAc/SS carrier DNA/PEG method," 2:35-37). The DNA construct was composed of genetic components described herein and assembled in plasmid vectors (e.g., pYES and pBSKII). Sequences of genes and/or proteins with desired properties were identified in GenBank; these included a histidine/phenylalanine ammonia lyase gene. These sequences were synthesized by CloneTex Systems, Inc. (Austin, Tex.). Other genetic parts were also obtained for inclusion in the DNA constructs including, for example, promoter genes (e.g. PAL promoter), reporter genes (e.g. cyan fluorescent reporter protein), terminator sequences, and regulatory proteins (e.g. ribosomal binding site). These genetic parts included restriction sites for ease of insertion into plasmid vectors.

PCR was used to enhance DNA concentration using a standard 5332. Eppendorf ThermoCycler (Eppendorf North America. 102 Motor Parkway, Hauppauge, N.Y., 11788) with specific sequence primers and the standard method for amplification (Sambrook, J., E. F. Fritsch, and T. Maniatis. 1989. Molecular cloning: A Laboratory Manual, 2nd ed., vol. 1. Cold Spring Harbor Laboratory Press, Cold Spring Harbor, N.Y.). Digestion and ligation were used to ensure assembly of DNA synthesized parts using restriction enzymes and reagents (PCR master mix, restriction enzymes: XhoI, KpnI, XbaI EcoRI, BamHI and HindIII, Alkaline Phosphatase and quick ligation kit, all from Promega). DNA was quantified using a NanoVue spectrophotometer (GE Life Sciences), and also a UV/visible spectrophotometer using the ratio of absorbances at 260 nm versus 280 nm. In order to verify final ligations, DNA was visualized and purified with electrophoresis using standard Thermo EC-150 power supply.

The DNA construct was made with different gene parts having different sequence sizes of from 30 bp to 1000 bp, including gene parts fundamental for expression such as, for example, ribosomal biding sites, native and constitutive promoters, reporter genes, and transcriptional terminators or stops. Backbone plasmids and synthetic inserts can be mixed together for ligation purposes at different ratios ranging from 1:1, 1:2, 1:3, 1:4, and up to 1:5 were evaluated. In one aspect, the ratio of backbone plasmid to synthetic insert is 1:4. After the vector comprising the DNA construct has been produced, the resulting vector can be incorporated into the host cells using the methods described below.

The DNA construct for phenolic compound induction ("the phenolic DNA") was constructed by assembling a plasmid (PBSKII) having the genetic components in the following order: (1) PAL promoter (SEQ ID NO. 1), (2) gene that expresses histidine/phenylalanine ammonia-lyase (SEQ ID NO. 5), (3) ribosomal switch RpoS (SEQ ID NO. 11), (4) ribosomal binding site (SEQ ID NO. 8), and (5) terminator (SEQ ID NO. 10). In certain embodiments, the reporter protein (SEQ ID NO. 15) that produces fluorescence can be added in between the ribosomal binding site and the terminator. The amount of fluorescence correlates to metabolite production in tissues and media. This phenolic DNA was transformed into cells as described below to produce the biological devices. A plasmid containing the phenolic DNA is shown in FIG. 1.

Host Cell Purification and Transformation

Established laboratory procedures were followed for yeast transformations (see Gietz and Schiestl, 2007). Yeast (*Saccharomyces cerevisiae* ATCC 200892) or bacteria cells such as *Escherichia coli* (TOP10 or DH10B™ chemically competent cells from Life Technologies™) or *Bacillus pumilus* (ATCC 8471) were transformed with the phenolic DNA. Host cells were in some cases isolated as entophytes from fruits and plant tissues. Fruits and plant tissues were disinfected under full aseptic conditions in a laminar flow cabinet and placed in a solution of ethanol (70%) for two minutes, then in sodium hypochlorite (5%) for two minutes, then rinsed three times with sterile distilled water. Dilution of disinfected samples and slices of samples were placed in different selective and non-selective media for bacteria and yeast and place under anaerobic or aerobic conditions. After incubation, different bacteria and yeast were isolated. After pathogenesis assays, the cells that were less pathogenic were selected as ideal host cells for plant tissue induction. Cells selected were identified by ribosomal RNA gene sequencing. Identified bacteria were purchased from ATCC.

Transformation proceeded according to manufacturers' protocols. In the case of *E. coli*, chemical transformation was performed. The yeast devices were made competent and transformed by the methods disclosed in Gietz, R. D. & R. H. Schiestl, 2007. *Bacillus pumilus* transformation was accomplished by electroporation of competent cells using 1.25 V/mm for 3.9 seconds and recovering the cells with 1 ml of thioglycolate broth enriched with 250 mM sucrose, 1 mM $MgCl_2$, and 5 mM $MgSO_4$ for an hour at 30° C. and plated on Muller Hilton agar with ampicillin Cells were made competent by a new chemical treatment preparation with an electroporation buffer containing 0.5 M HEPES, 0.5 M sucrose, glycerol at 80%, and 25 mM of $MgCl_2$. The buffer was added to pelleted cells after overnight growth in aseptic conditions at a temperature of 4° C. The pellet was centrifuged and washed three times with the buffer, aliquotted, and used immediately or stored at −80° C.

DNA expression and effectiveness of transformation were determined by fluorescence of the transformed cells expressed in fluorescence units (FSUs), according a protocol provided by the manufacturer, using a 20/20 Luminometer (Promega). The blue fluorescence module using the 450/600 nm wavelengths was used to evaluate the effectiveness of transformation. Plasmid DNA extraction purification, PCR, and gel electrophoresis were also used to confirm transformation.

Different transformed devices were obtained. Different types of fluorescent reporter proteins were used (yellow fluorescent protein, red fluorescent protein, green fluorescent protein, and cyan fluorescent protein) for all transformed cells or devices. However, the cyan fluorescent protein was preferred. When no fluorescent reporter protein was assembled, no fluorescence was observed.

Chitosan

Chitosan is a natural linear polysaccharide compound composed of randomly distributed β-(1-4)-linked D-glucosamine and N-acetyl-D-glucosamine residues. To produce chitosan, chitin was first extracted from the exoskeletons of crustaceans (e.g., shrimp and/or crabs). Samples were treated variously with inorganic acid (to demineralize), sodium hydroxide (to remove proteins), and organic solvents (to remove lipids and other hydrophobic components). Chitin was deacetylated to produce chitosan (degree of acetylation approximately 70-80%), again using sodium hydroxide. Here, the chitosan was dissolved in glacial acetic acid and used as a concentrate of 1%.

Mature Cocoa (*Theobroma cacao*) Fruits were Used as Source of Embryonic Cells for the Development of the Calluses Mature cocoa fruits were first subjected to surface disinfection by using a soapy water solution and followed by treatment with iodine solution (3 mg/L) for 15 minutes. Then, disinfection of the cocoa seeds (grains) was performed by treating the seeds with ethanol solution (70%) for 3 minutes, followed by treatment with sodium hypochloride solution (1%) for 10 minutes. Finally, the seeds were washed three times with sterile distilled water. The surface disinfection process was performed inside a laminar flow cabinet under aseptic conditions.

After surface sterilization, seeds (grains) were subjected to induction of calluses in specific media for tissue cultures as follows (see Murashige, T. and Skoog, F. "A revised medium for rapid growth and bioassays with tobacco tissue cultures," *Physiologia Plantarum*, 1962, Vol 15: 473-495). Disinfected cocoa seeds were submitted to extraction of embryonic cells under aseptic conditions, and transferred to growth medium (MS), which contains mineral salts and microelements, and which is enriched with myo-inositol (100 mg/L) and sucrose (30 g/L), with gellan gum (2.4 g/L) as a gelling agent. The cocoa explants were incubated under dark conditions for 7 days at 22-24° C. After the incubation period, the cocoa embryonic cells were subcultured in nutrient media with the same types of ingredients as the media mentioned above, but containing different concentrations of auxins (growth hormones 2,4-D), using four different concentrations (0, 0.1, 0.5, 1.0 and 2.0 mg/L). A random experimental design was used with three replicates and 10 experimental units during 100 days at 22-24° C.

Standard media for growing calluses was used during the investigation (Table 1). The main media was prepared based on standard MS media supplemented with sucrose (30 g/L). The media included a gellan gum base (2.4 g/L) and was prepared at pH 5.8. All cultured calluses were incubated in dark conditions at 25° C. Data were subjected to statistical analysis including ANOVA and level of significance.

TABLE 1

Composition of the media or induction of cocoa callus.

| Salt Solution | Stock Concentration (g/L) | Volume of Stock (mL/L) | Final Concentration (mg/L) |
| --- | --- | --- | --- |
| $NH_4NO_3$ | 82.50 | 20 | 1650 |
| $KNO_3$ | 95.00 | 20 | 1950 |
| $H_3BO_3$ | 1.24 | 5 | 6.20 |
| $KH_2PO_4$ | 34.00 | | 170 |
| KI | 0.166 | | 0.83 |
| $Na_2MoO_4 \cdot 2H_2O$ | 0.05 | | 0.25 |
| $CoCl_2 \cdot 6H_2O$ | 0.005 | | 0.025 |
| $CaCl_2 \cdot 2H_2O$ | 88.00 | 5 | 440 |
| $MgSO_4 \cdot 7H_2O$ | 74.00 | 5 | 370.0 |
| $MnSO_4 \cdot H_2O$ | 3.38 | | 16.9 |
| $ZnSO_4 \cdot 7H_2O$ | 1.72 | | 8.6 |
| $CuSO_4 \cdot 5H_2O$* | 0.005 | | 0.025 |
| $Na_2 \cdot EDTA$ | 7.45 | 5 | 37.25 |
| $FeSO_4 \cdot 7H_2O$ | 5.57 | | 27.85 |
| Myo-inositol | 20 | 5 | 100 |

Increase of Cellular Mass of the Calluses by Using Growth Regulators

Different concentrations including 0, 0.1, 0.2, 0.5, 1, 2, 4, mg/L of kinetin were evaluated. Also, kinetin was used with or without 2,4-D at concentration of 2 mg/L. The growth of calluses was evaluated after 100 days, and different parameters were used to determine the effects of the growth regulators on callus growth including % of disaggregation and height and diameter of the callus. A ransom bifactorial design was used with 10 experimental units. Each experiment was replicated three times. All experiments were conducted following standard methods of tissue culturing, as described above.

Three different clones of cocoa at different ages (Table 2) were used during the investigation in order to determine their effects on development of calluses in relation to potential production of polyphenolic compounds.

TABLE 2

Different clones of cocoa at different ages used to induce callus development.

| Cocoa CLONE (variety) | Age of Cocoa Fruit (days) |
| --- | --- |
| CCM 51 | 40 |
| | 80 |
| | 120 |
| TSH 565 | 40 |
| | 80 |
| | 120 |
| ICS 60 | 40 |
| | 60 |
| | 120 |

Effects of Phenotype and Age of the Cocoa Fruit on Callus Development

Table 3 shows the positive effect of 2,4-D on stimulating growth of cocoa callus at early stages of development. The growth regulator 2-4-D at concentration of 2 mg/L induced larger growth in cocoa calluses. This effect was observed for all three cocoa phenotypes used. Also, this positive effect was bigger in mature cocoa fruits (20 days old).

TABLE 3

Effects of 2,4-D growth regulator alone or in combination with chitosan on initial callus development of three different cocoa phenotypes.

| Treatment mg/L | % of Callus Development |
| --- | --- |
| 2,4 D (A) | |
| 0 $mgL^{-1}$ | 7.63889 |
| 2 $mgL^{-1}$ | 22.9167 |
| Standard Error | 3.72678 |
| Chitosan (B) | |
| 0.1 wt % | 2.22222 |
| 0.02 wt % | 8.05556 |
| 0.05 wt % | 12.7778 |
| 0 wt % | 38.0556 |
| Standard Error | 5.27046 |
| Age (C) | |
| 40 days | 7.91667 |
| 80 days | 13.3333 |
| 120 days | 24.5833 |
| Standard Error | 6.45497 |
| Clone (D) | |
| TSH | 10.8333 |
| ICS | 14.5833 |
| CCM | 20.4167 |
| EE | 4.56762 |
| Factor A | DS |
| Factor B | DS |
| Factor C | DS |

TABLE 3-continued

Effects of 2,4-D growth regulator alone or in combination with chitosan on initial callus development of three different cocoa phenotypes.

| Treatment mg/L | % of Callus Development |
| --- | --- |
| Factor D | NS |
| Interaction of ABC | DS |

Use of Chitosan to Induce Phenolic Compounds During Early Callus Growth

Chitosan treatment alone induced higher production of polyphenolic compounds in the early stages of callus growth. This effect was observed in the agar media where the callus was growing. This effect was more pronounced, however, during the later stages of callus development (e.g., after three weeks).

Chitosan was used in both the induction of calluses within one week, and the growth of calluses and production of phenol compounds after 2 weeks of callus development. Chitosan was first applied during the induction of the growth of the callus, and during the first week in order to stimulate aggregation of callus cells. The concentration of chitosan used depended upon the type of callus clone and size. Thus, different concentrations of chitosan were used: 0, 0.02, 0.05, 0.1, 0.2, 0.5, and 1.0 ppm. Chitosan was added to the medium in Petri dishes. Chitosan was also used with or without the conventional growth regulator 2,4-D at the concentrations mentioned previously (0, 0.1, 0.2, 1, and 2 mg/L).

Chitosan was also used after 2 weeks of callus development in order to enhance production of phenol compounds. Chitosan was applied by spreading or injection. Different volumes of the chitosan solutions were used including 10 µL, 50 µL, 100 µL, and 1 mL, depending on the size of the callus.

Inoculation of Callus with Phenolic Devices

Three week old calluses made from somatic cells of cocoa (*Theobroma cacao*) were inoculated with two phenolic devices. Calluses were pretreated with chitosan at 0.1% prior to treatment with the phenolic devices. Calluses were used at different stages of growth, including 1, 2, 3, 4, 5, and 6 weeks old from the first day of growth, with 5 week-old calluses being preferred. Selected calluses were inoculated with phenolic devices that were 48 hours old. Different dilutions of phenolic devices (i.e. $10^3$, $10^4$, $10^5$, $10^6$, and $10^9$ cells/mL) were used, with $10^3$, $10^6$, and $10^9$ cells/mL being preferred. Inoculation of bacterial devices into the calluses was performed by spreading or by injection using different volumes of the device, including 10, 50, 100, 300, or 500 µL, with inoculation by injection using a volume of 150 µL was preferred. Two bacterial devices were evaluated: (1) transformed *B. pumilus* containing the sequence PAL+PAL promoter+Ribosomal binding site+transcriptional stopper (phenolic device II), and (2) same as #1 plus a fluorescent reporter protein, but assembled in *E. coli* (phenolic device I).

After inoculation of the calluses with the phenolic devices, the calluses were subjected to evaluation of the production of phenolic compounds including polyphenolic compounds. Different parameters were used to assess production of polyphenolic compounds in calluses:

1. Growth of calluses, determined by size and biomass weight.
2. Color and texture of the calluses. This was determined by observation directly with the naked eye and by photographic observation
3. Production of phenolic compounds including polyphenolic compounds. This was determined by presence of phenolic compounds in the agar media where calluses were growing, and by chemical analytical by extraction and HPLC quantification following standard procedures as described below.
4. Concentration of the transformed bacteria used to inoculate the calluses were also determined by standard microbiological methods such as counting colony forming units (CFUs) and measuring optical density (OD) using a UV/visible spectrophotometer set at 600 nm wavelength.

All experiments were done in 3-6 replicates. Mean and standard deviation (SD) were calculated for each experiment.

The main parameters used for assessing production of polyphenolic compounds in calluses were:

1. Growth of callus. This was done by determining the weight of the biomass and the size of the callus.
2. Texture of the callus by touch under aseptic conditions.
3. Color of the callus. This was done a relative arbitrary observation scale between light brown to dark brown, since all calluses are brown during this phase of development. Pictures were taken during this phase.
4. Production of phenolic compounds including polyphenolic compounds was determined by extraction or digestion, and quantified by HPLC. Also, observation of presence of brownish color in the agar media where the calluses were grown was recorded as an indication of production of phenolic compounds including polyphenolic compounds.
5. Determination of the concentration of bacterial cells of the phenolic devices used to inoculate the calluses. This was performed by standard microbiological methods, with dilution, when necessary, to determine the colony forming units (CFU) and/or by optical density (OD) spectrophotometrically at 600 nm.
6. Assessment of these parameters was carried out daily and/or weekly. Also, total DNA and RNA, and fluorescence of the devices were determined, in order to assess the genetic fitness of the devices containing the phenolic DNA PAL proteins and/or other genes encoding for the proteins responsible for the production of the phenolic compounds, including polyphenolic compounds. Standard molecular biology and synthetic biology procedures were used (Cuero et al. "Constructed Microbial Sensor to Enhance Detection of Metals" *Journal of Biotechnology* 2012, Vol 158: 1-7).

Expression of the proteins and/or enzymes responsible for production of polyphenolic compounds was determined by both real-time PCR (qPCR and 2D DIGE separation followed by mass spectrometric analysis.

Figure 3:
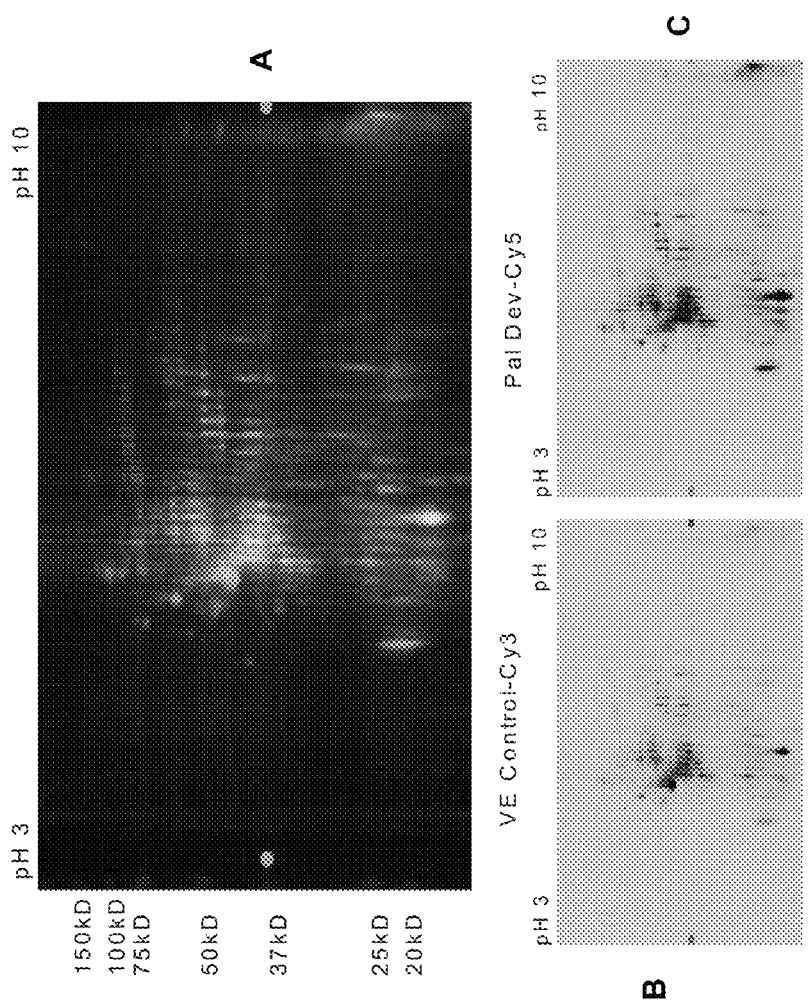
FIG. 3 shows the expression of proteins in a two-dimensional 2D-DIGE gel, in which a protein gel of *B. pumilus* device has been overlapped with a control gel (non-transformed bacterium). Picture shows higher expression of up-regulated proteins (higher intensity fluorescence points) corresponding to *B. pumilus* device containing the phenolic DNA with PAL protein (see panel C) contrasted with a control (see panel B), which showed down-regulated proteins and reduced fluorescence. The analysis was done with MALDI-MS.
Figure 4:
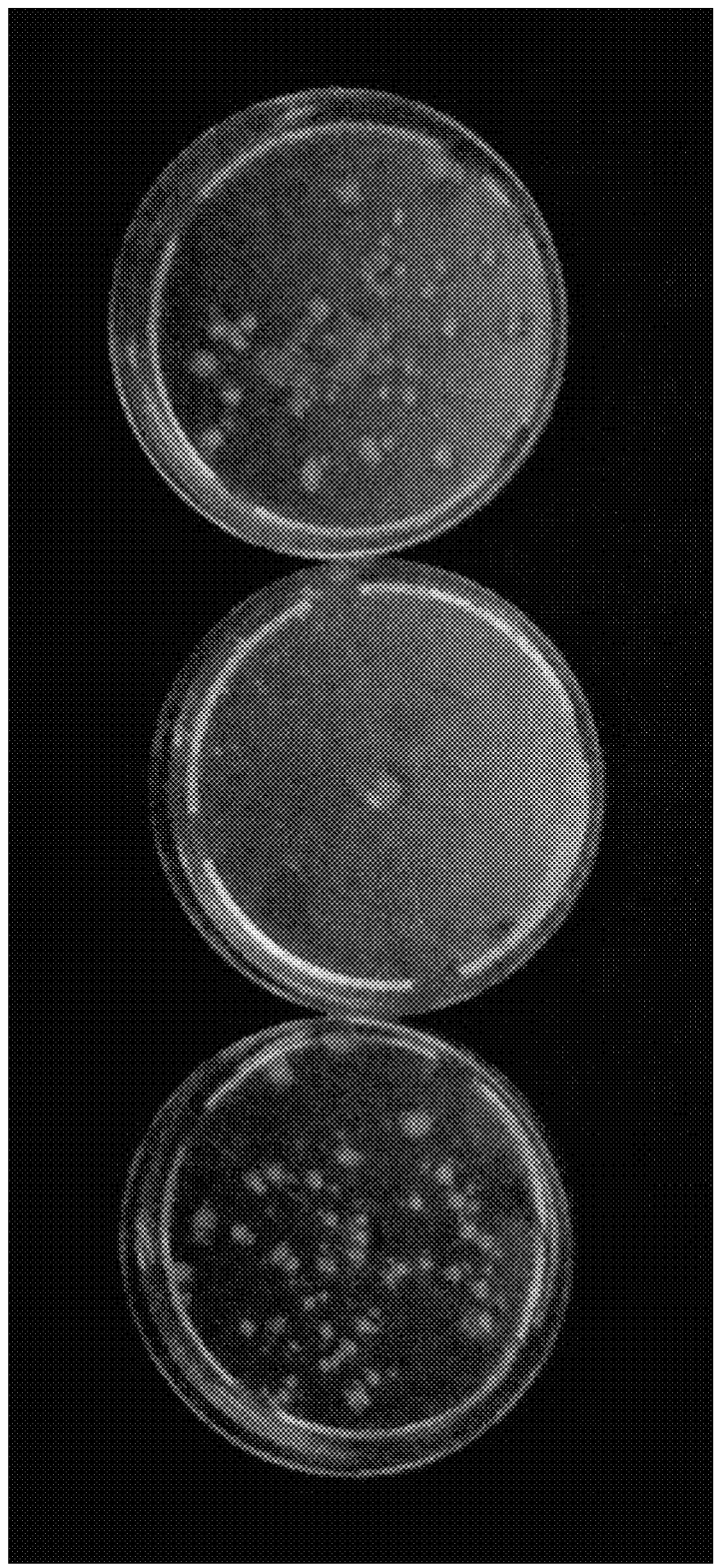
FIG. 4 shows colonies of *E. coli* devices. B: control (bacteria without phenolic DNA) shows less colony formation than A and C, which are bacterial devices containing phenolic DNA. In A and C, the colony populations completely cover the agar plates.
Figure 5:
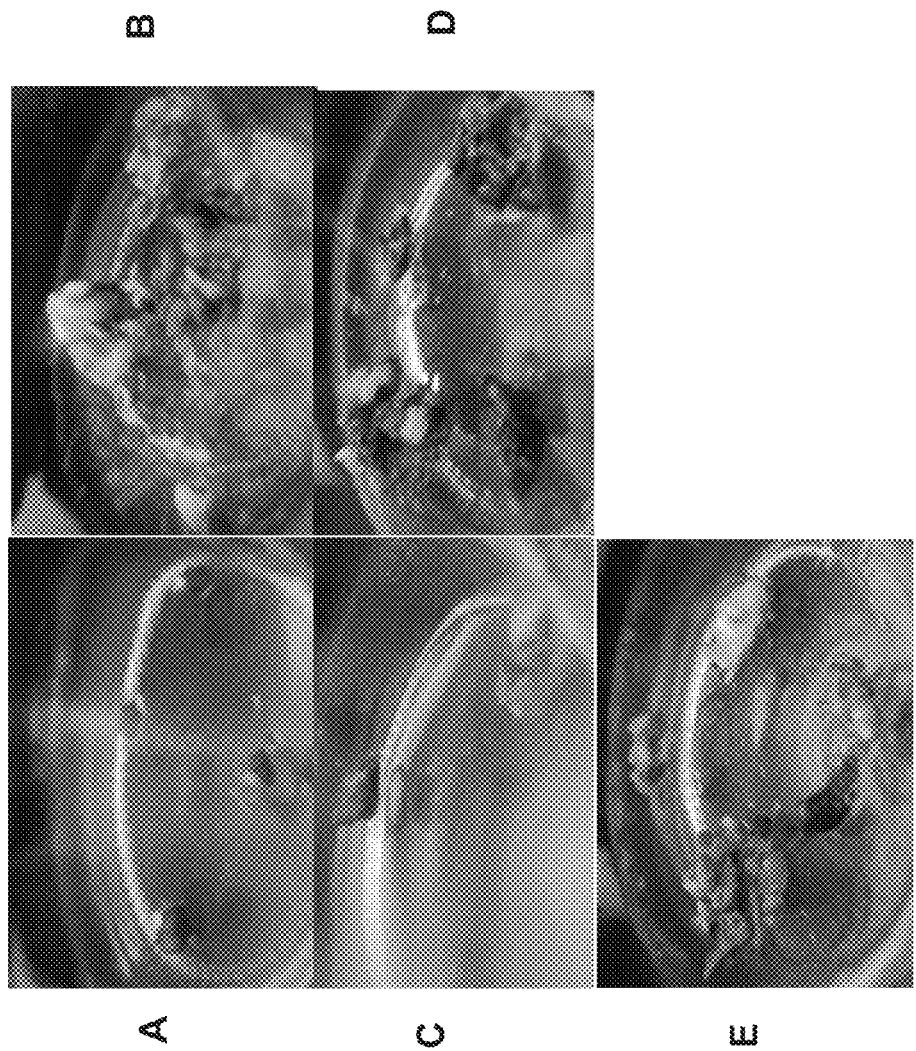
FIGS. 5A-5E show cocoa embryonic calluses grown in Murashige-Skoog (MS) medium under the following conditions: (A) no treatment with bacterial device containing phenolic DNA (control); (b) treatment with *B. pumilus* ($10^3$ cells/mL) transformed with phenolic DNA; (c) treatment with *B. pumilus* ($10^6$ cells/mL) transformed with phenolic DNA; (d) treatment with *B. pumilus* ($10^9$ cells/mL) transformed with phenolic DNA; and (b) treatment with *E. coli* ($10^6$ cells/mL) transformed with phenolic DNA.

FIGS. 2-5 and Table 4 show the efficacy of the assembly of the PAL gene and other genetic parts in vector pYES in bacteria *E. coli* and *B. pumilus*, respectively. The figures show abundant growth of the phenolic devices that would eventually be inoculated into the calluses. Thus, more growth of the phenolic devices (i.e., colonies) represented greater expression of the protein PAL, which was responsible for the production of polyphenolic compounds. FIG. 3 and Table 4 corroborate the high production of proteins related to the production of polyphenolic compounds. Brighter spots in FIG. 3 represent expression of some proteins; these proteins are listed in Table 4.

Phenolic devices I and II showed higher induction of polyphenolic compounds than the control (*E. coli* or *B. pumilus* without transformation). Results from qPCR corroborate the correlation between higher production of phenolic compounds and higher gene expression in the bacterial devices (transformed bacteria) as compared to controls (non-transformed bacteria).

FIG. 3 and the tables below show the high correlation between gene and protein expression and the higher production of phenolic compounds in callus inoculated with bacterial devices assembled with the protein PAL and other genetic parts as compared to control (callus inoculated with bacteria not containing PAL genes or other assembled genetic parts). The tables below also show higher DNA expression in phenolic devices containing PAL protein, especially of genes encoding for proteins related to the production of phenolic compounds. Likewise, FIG. 3 and Table 4 show a higher expression of proteins related to production of phenolic compounds.

TABLE 4

Proteins that were highly expressed and identified in the phenolic devices assembled with PAL protein in relation to production of phenolic compounds in untreated cocoa calluses.

| Protein/Enzyme | Function |
|---|---|
| GroEL | Protein complex that is involved in plant stress. |
| Subtilisin | Non-specific protease which breaks peptide bonds and participates in synthesis of other proteins. |
| Carboxylesterase | Catalyzes the hydrolysis of esters and amide groups; also is involved in metabolism of aromatic compounds. |
| ORF6 | Thioesterase involved in plant-bacteria interaction, symbiosis, conjugation, and genetic regulation. |
| 2-keto-3-deoxy-D-arabinoheptulosonate-7-phosphate synthase | Catalyzes the initiation of biosynthesis of aromatic amino acids through condensation of phosphoenolpyruvic acid and erythrose-4-phosphate. |
| Anthranilate phosphoribosyl-transferase | Catalyzes an early reaction of tryptophan synthesis; condenses one molecule of 5-phosphoribosyl-α-pyrophosphate with one molecule of anthranilate and releases inorganic phosphate. |
| α-L-arabinosidase | Glycosidase that hydrolyzes α-L-arabinofuranosides; also involved in the mechanism of response of a plant to microorganisms. |
| Putative chitinase | Involved in breaking glycosidic bonds and allowing release of carbohydrates from plant cells in relation to production of secondary metabolites. |

TABLE 5

RNA Production from *B. Pumilus* phenolic device as compared to control (Non-transformed *B. pumilus*). Measurements were done in a spectrophotometer at 260/280 nm.

| Sample | Undiluted RNA (ng/μL) | A260 | A280 | 260/280 |
|---|---|---|---|---|
| Control | 74.3 | 0.223 | 0.112 | 1.99 |
| Experimental | 488.8 | 0.611 | 0.295 | 2.07 |

TABLE 6

Results of time PCR (qPCR) showing expression of genes that encode for PAL protein (standardized).

| Gene | Control | Experimental |
|---|---|---|
| PAL | 1 | 1.27 |

Effect of Concentration of Phenolic Device on Induction of Phenolic Compounds in Cocoa Callus The efficacy of the methods disclosed herein was also clearly observed when using different populations of phenolic devices. Different concentrations of bacterial devices were used, including $6\times10^5$, $2\times10^4$, $1\times10^3$, and 100 cells/mL. However, the first three dilutions were most effective concentration in inducing production of phenolic compounds in cocoa callus.

FIGS. 5A-5E show the strong effect of the *B. pumilus* phenolic device with the PAL sequence at concentrations of $10^3$, $10^6$ and $10^9$ cells/mL (FIGS. 5B-5D, respectively) on both growth and production of phenolic compounds in cocoa calluses compared to untreated callus (FIG. 5A). Likewise, the *E. coli* phenolic device containing the PAL sequence at a concentration of $10^6$ cells/mL (FIG. 5E) showed a strong effect on both growth of cocoa calluses and production of phenolic compounds compared to the control in FIG. 5A. Presence of phenolic compounds is seen by the naked eye on the surface of the agar, and the concentrations in calluses can be easily quantified by HPLC.

Extraction and Quantification of Polyphenolic Compounds from Cocoa Calluses

Standard protocols for the extraction of phenolic compounds including polyphenolic compounds were followed. The Folin-Ciocalteau (Singleton, V L, Orthofer, R, Lamuela-Raventos, R M., 1999, "Analysis of total phenols and other oxidation substances and antioxidants by mean of Folin-ciocalteau reagent," *Methods Enzymol.*, 299:152-178; Ebel, J., 1986, "Phytoalexin synthesis: the biochemical analysis or the induction process," *Ann Rev. Phytopathol.* 24:235-264; Mansfield, J. W., 1983, "Antimicrobial compounds," In: *Biochemical Plant Pathology, Ed: J. A. Callow, New York: John Wiley and Sons, Ltd. Pp.* 237-265). An HPLC method was used to identify and quantify the phenolic compounds, including polyphenolic compounds (C. Stalikas, 2007, "Extraction, Separation, and Detection Methods for Phenolic Acids and Flavonoids," *J. Sep. Sci.*, 30:3268-3295).

Extraction and quantification of phenolic/polyphenolic compounds were carried out on calluses after 15 days of treatment with or without bacterial devices, as follows:
1. Maceration of callus biomass mixed with different concentrations of acetone at 50%, 60%, 70%, 80%, 95%, with 70% preferred.
2. Liquid extract from above was subjected to electrical homogenization at different shaking speeds including 50, 90, 100, 200, and 300 rpm, with 90 rpm preferred.
3. Filtration and centrifugation. Centrifugation was carried out at 9000 rpm at 4° C. for 10 minutes.
4. Rotoevaporation was performed in order to eliminate remaining acetone from the solution, thus obtaining an aqueous solution for the final analysis of phenolic/polyphenolic compounds by HPLC
5. Identification and quantification of phenolic/polyphenolic compounds by HPLC.

Extracted polyphenolic compounds were first quantified by the method of Folin-Ciocalteau using a UV/visible spectrophotometer, and the results were expressed based on gallic acid (GA) in dried weight of biomass and without fatty material.

Identification and Quantification of Polyphenolic Compounds Using Reverse Phase HPLC Extracted phenolic compounds were subjected to identification for polyphenolic compounds using an HPLC method. Different standards of phenolic compounds were used for the HPLC analysis. The retention times of the standards in the HPLC were compared with the retention times of the extracted phenolic compounds, which were also injected into the HPLC under similar HPLC operational conditions. Then, quantitative results between standards of phenolic compounds and phenolic compounds extracted from calluses were compared. Different standards of polyphenolic compounds were used, including: caffeic acid, catechins, p-coumaric acid, gallic cid, p-hydroxybenzoic acid, and vanillic acid.

The above-mentioned phenolic compounds were used for the internal calibration curve of the HPLC following a standard procedure for HPLC calibration. Phenolic samples and standards were filtrated before injected into the HPLC. A 10 μL injection volume was used; two replicates of each sample were injected. Flow rate was 1 mL/min and the detector wavelength was 210 nm.

Mobile phase A: deionized water with phosphoric acid (0.1%); mobile phase B: acetonitrile with phosphoric acid (0.1%). Total time of running was 35 minutes, distributed as follows: 0-22 minutes 95% A, 5% B; 22-29 minutes 90% A, 10% B; 29-30 minutes 80% A, 20% phase B; 30-35 minutes 95% A, 5% B.

Extraction, Identification, and Quantification of Polyphenolic Compounds from Cocoa Calluses Extraction of polyphenolic compounds from the calluses was easier and more cost-efficient when compared to conventional methods that use cocoa seeds, where there is need to eliminate more plant biomass and fatty material. Most cocoa seeds or grains contain between 13-55% fatty material, which requires the use of more chemical solvents for extraction. However, extraction of polyphenolic compounds from cocoa calluses using the methods described herein does not require the elimination of the fatty materials. Additionally, the callus biomass is smaller and softer than cocoa seeds. Thus, the current methods are more cost-efficient, more time efficient, and more energy efficient (no heat is required for extraction of polyphenolic compounds).

Analysis of the polyphenolic compounds from cocoa seeds or grains was also carried out by the Folin-Ciocalteu method using a UV/visible spectrophotometer, based on gallic acid equivalents (EAG). Thus, data are provided based on the equivalent to gallic acid/100 g of dry mass of sample, where the calluses were dried and pulverized before being subjected to analysis of polyphenolic compounds following standard protocols.

Cocoa seeds or grains were first subjected to the elimination of fatty material (comprising 45-65% of the seeds). The process was performed using n-hexane solvent. The extraction of fatty material was performed three times in order to eliminate enough fat to avoid interference with the quantification of polyphenolic compounds using standard procedures.

Provided below is a description of an exemplary extraction process used herein:
1. Extraction of polyphenolic compounds from cocoa seeds with mixture of acetone/water (70:30, 60:40, 50:50), with 70:30 being preferable.
2. Shaking at ambient temperature (26° C.).
3. Filter; the filtrate is washed with deionized water then saved for next step.
4. The material obtained is subjected to rotoevaporation to eliminate acetone residues and produce an aqueous solution.
5. All solutions were standardized by volume, then subjected to the Folin-Ciocalteu test and analyzed in the spectrophotometer as described above.
6. Purified samples were quantified under spectrophotometer at 765 nm.

A standard curve based on gallic acid at concentrations between 2 and 14 ppm using Beer's Law was performed in order to carry out the Folin-Ciocalteu analysis of polyphenolic compounds.

Concentrations of polyphenolic compounds were determined spectrophotometrically based on absorbance (A) using the equation below with a correlation coefficient of ($r^2$) of 0.99915, and the constant k1 which is equal to 10.099. A is the absorbance of the samples:

$$c = k1 \times A$$

Final results are expressed on percentage of polyphenolic compounds, using the equation below:

$$\% \text{ Polyphenols} = \frac{\text{concentration}\left(\frac{mg}{L}\right) \times \text{Volume }(L) \times FD}{\text{sample weight (mg)}} \times 100$$

The percentage of polyphenolic compounds is expressed on EAG/100 g sample as described above. The final concentration is obtained when the absorbance of the samples obtained crosses with the standard curve of gallic acid described above. FD is the dilution factor, the volume (L) is the aliquot used for the Folin-Ciocalteu analysis. Results are provided in Table 7.

TABLE 7

Concentration of polyphenolic compounds in cocoa calluses after spectrophotometer analysis.

| Treatment | Variety of Cocoa | Weight of sample (mg) | % Total Polyphenolics (EAG/100 g) | SD |
|---|---|---|---|---|
| CONTROL callus | ICS | 512 | 7.35 | 0.03321 |
| Device (Construct PAL $10^9$ B. pumilus | CCM | 418 | 47.51 | 0.01848 |
| Cocoa fruit 1 | | 10000 | 11.06 | 0.3564 |
| Cocoa fruit 3 | | 10000 | 14.57 | 0.00434 |

NOTE:
After 20 days of growth, cocoa calluses were inoculated with phenolic devices (B. pumilus). Analysis was performed 15 days after inoculation.

Quantification of Polyphenolic Compounds by Reverse Phase HPLC

HPLC analysis and quantification of the polyphenolic compounds was done using a standard curve based on pure standards of polyphenolic compounds and determining their retention time (RT). Results show high production and purity of the free polyphenolic compounds from the samples of cocoa calluses.

Five different concentrations for each polyphenolic compound were used during the analysis by reverse phase HPLC, as follows:
1. Retention time for each standard was determined by the HPLC.
2. Mixtures of standards of polyphenolic compounds were also run through the HPLC in order to make sure that the polyphenolic compounds of interest were not hidden by other compounds, since some of them show some molecular similarities.
3. Samples extracted from cocoa callus that were purified were then analyzed by HPLC.
4. Data was analyzed taking into consideration the dilution of the extracts from the calluses, the concentration obtained by HPLC, and the dilution of the samples that were injected. The following equation was used:

$$\% \text{ Phenolic acid} = \frac{\text{concentraiton } HPLC \left(\frac{mg}{L}\right) \times \text{Volume } (L) \times FD}{\text{sample weight (mg)}} \times 100$$

5. Results were expressed in relation to the corresponding standards and are provided in Table 8.

TABLE 8

Quantification of polyphenolic compounds from cocoa calluses using reverse phase HPLC.

| Treatment | Cocoa Variety | p-Coumaric Acid % p-CA | SD | Gallic Acid % p-GA | SD | p-Hydroxy-benzoic Acid % p-HA | SD | Catechin % p-CAT | SD | Average Total % | SD |
|---|---|---|---|---|---|---|---|---|---|---|---|
| Control (1) | ICS | 1.37 | 0.81 | 0 | 0 | 1.93 | 0.03 | 0.36 | 0.17 | 0.85 | 0.33 |
| Control (2) | CCM 51 | 0.53 | 0.155 | 2.98 | 0.014 | 0.79 | 0.0091 | 0 | 0 | 1.43 | 0.0594 |
| $10^6$ B. pumilus (3) | ICS | 0 | 0 | 7.75 | 0 | 0 | 0 | 0 | 0 | 7.75 | 0 |
| Chitosan + PAL $10^6$ B. pumilus (4) | TSH | 0 | 0 | 0 | 0 | 2.18 | 0.0075 | 0 | 0 | 2.18 | 0.0075 |
| PAL $10^6$ B. pumilus (5) | CCM 51 | 2.51 | 0 | 7.75 | 0 | 0.8 | 0.0091 | 0 | 0 | 3.69 | 0.003 |
| COCOA 2 | CCM 51 | 2.58 | 0.05 | 2.02 | 0.086 | 0 | 0 | 1.53 | 0.009 | 2.04 | 0.0489 |
| COCOA 3 | ICS | 8.4 | 7.49 | 0.97 | 0.14 | 1.58 | 0.01 | 2.77 | 0 | 3.43 | 1.9105 |

(1) Treatment Control 1 = ICS callus alone without treatment.
(2) Treatment Control 2 = CCM 51 callus alone without treatment
(3) Callus + Device B. pumilus ($10^6$)
(4) Callus + Device B. pumilus ($10^6$) + chitosan
(5) Callus + Device B. pumilus ($10^6$)
Note:
Production of phenolic compounds was also determined in agar using only the ICS variety. Only p-hydroxybenzoic acid was produced in agar, at 1.17% (SD = 5.05).

In Vivo Antimicrobial Test of Polyphenolic Compounds in Cocoa Fruits

The objective was to demonstrate the efficacy of the polyphenolic compounds isolated from the cocoa calluses for controlling common diseases in cocoa plants, including the fruits. Forty-day-old cocoa fruits were inoculated with fungus *Moniliophthora roreri*, which is a common pathogen of cocoa crops. Different concentrations of polyphenolic compounds extracted from cocoa callus, as described above, were used in order to control *M. roreri* in infected cocoa fruits.

Cocoa fruits were surface disinfected with alcohol (70%) and sodium hypochlorite (1%) and washed with sterile water following standard procedures. Next, cocoa fruits were inoculated with solutions of *M. roreri* using a dilution of $10^3$ spores/mL, as follows:
  Treatment 1: Untreated Cocoa (Control).
  Treatment 2: Cocoa fruits+Fungal solution.
  Treatment 3: Cocoa fruits+Fungal Solution+Polyphenolic Solution.
  Treatment 4: Cocoa fruits+Polyphenolic solution alone.
  Treatment 5: Cocoa fruits+fungal solution applied after three days of phenolic solution application.

All fungal solutions were mixed with polysorbate 20 solution as carrier, thus ensuring efficacy of spreading the fungal solution over the surfaces of the cocoa fruits. Treatment was done by immersion of the cocoa fruits into solutions of polyphenolic compounds at concentration equivalent to 0.028 EAG/g of sample. All treatments were placed in sterile desiccators and incubated in an environmental chamber set at 26° C. and 99.7% relative humidity for ten days.

The polyphenolic compounds produced by calluses using the phenolic devices effectively controlled the growth of fungus including *M. roreri* on cocoa fruits. Treatment inhibited completely any fungal growth on the cocoa fruits, and also enhanced the physical characteristics of the fruits, such as freshness and turgidity. Thus, the phenolic compounds produced by the phenolic devices enhance the organoleptic properties of the cocoa fruits. Therefore, the polyphenolic compounds can be used to enhance storage quality in cocoa and any other fruit by enhancing freshness and/or organoleptic properties of the fruit.

Uptake of Phenolic Devices by *Theobroma cacao*

Figure 6:
FIG. 6 shows cocoa (*Theobroma cacao*) callus from tissue culture assays. Induction of size increase in the calluses treated with chitosan and biological devices is also shown.

FIG. 6 and Tables 10 and 11 below summarize the results of using the methods described herein for producing phenolic compounds from cocoa. FIG. 6 shows cocoa (*Theobroma cacao*) callus from tissue culture assays. The phenolic device II was used in these experiments (*B. pumilus* transformed with phenolic DNA). The use of chitosan and device II significantly increases the size of the cocoa callus.

Table 10 shows the fluorescence of the reporter protein of the phenolic devices I and II injected in cocoa (*Theobroma cacao*) callus compared to callus not treated with the cells (control). The fluorescence confirms that the microbial cells were well transformed and the phenolic DNA taken up in the cultured calluses. Table 11 shows RNA and DNA concentrations extracted from cocoa (*Theobroma cacao*) callus of treated and non-treated (control) tissue cultures measured by nanospectrometry. The difference in concentrations demonstrates the genetic induction related to growth of tissue plant and production of phenolic compounds after treatment with chitosan and/or phenolic devices I and II. Results also show the benefits of using *B. pumilus* as the host cells, which is a naturally-occurring bacteria present in cocoa.

TABLE 10

Fluorescence of the reporter protein of the transformed cells injected in cocoa (*Theobroma cacao*) callus as compared to callus non-treated with the transformed cells (control).

|  | Control | Treated with Device II | Treated with Device II + Reporter |
|---|---|---|---|
| Fluorescence (FSUs) mean ± SD | 0.2 ± 0.03 | 310 ± 16.4 | 498 ± 14.5 |

TABLE 11

RNA and DNA concentrations extracted from Cocoa (*Theobroma cacao*) callus of treated and non-treated (control) tissue cultures, measured by nanospectrometry.

|  | Control | Treated with Phenolic Device I | Treated with Phenolic Device II |
|---|---|---|---|
| RNA (µg/µL) mean ± SD | 9.4 ± 0.3 | 47.5 ± 1.5 | 52.3 ± 0.2 |
| DNA (µg/µL) mean ± SD | 3.2 ± 1.1 | 9.3 ± 1.3 | 10.9 ± 2 |

Throughout this application, various publications are referenced. The disclosures of these publications in their entireties are hereby incorporated by reference into this application in order to more fully describe the compounds, compositions and methods described herein.

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary.

What is claimed:

1. A method for enhancing the production of phenolic compounds from a cocoa callus, the method comprising contacting the callus with a biological device comprising a DNA construct transformed in host cells, wherein the DNA construct comprises from 5' to 3' the following genetic components in the following order: a PAL, promoter having at least 90% identity SEQ ID NO: 1; a gene that expresses histidine/phenylalanine ammonia-lyase having, at least 90% identity of SEQ ID NO: 5; and a ribosomal switch having at least 95% identity of SEQ ID NO: 11, and wherein the sum of the phenolic compounds produced by the cocoa callus contacted by the biological device is greater than the sum of phenolic compounds produced by the cocoa callus that is not contacted by the biological device.

2. The method of claim 1, wherein the DNA construct is in a vector.

3. The method of claim 2, wherein the vector is a plasmid.

4. The method of claim 3, wherein the vector is PBSKII.

5. The method of claim 1, wherein the host cells comprise yeast or bacteria.

6. The method of claim 5, wherein the bacteria comprises *Bacillus pumilus* or *E. coli*.

7. The method of claim 1, wherein the callus is grown in chitosan prior to being contacted with the biological device.

8. The method of claim 7, wherein the chitosan is from 60% to 100% acetylated.

9. The method of claim 7, wherein the chitosan comprises from 3 to 20 glucosamine units and/or N-acetylglucosamine units.

10. A cocoa callus inoculated with a biological device comprising a DNA construct transformed in host cells, wherein the DNA construct comprises from 5' to 3' the following genetic components in the following order: a PAL promoter having at least 90% identity of SEQ ID NO. 1; a gene that expresses histidine/phenylalanine ammonia-lyase having at least 90% identity of SEQ ID NO. 5; and a ribosomal switch having at least 95% identity of SEQ ID NO. 11.

11. The callus of claim 10, wherein the DNA construct is in a vector.

12. The callus of claim 11, wherein the vector is a plasmid.

13. The callus of claim 11, wherein the vector is PBSKII.

14. The callus of claim 10, wherein the host cells comprise yeast or bacteria.

15. The callus of claim 14, wherein the bacteria comprises *Bacillus pumilus* or *E. coli*.

* * * * *

SEQUENCE LISTING

```
<160> NUMBER OF SEQ ID NOS: 15

<210> SEQ ID NO 1
<211> LENGTH: 540
<212> TYPE: DNA
<213> ORGANISM: Abies grandis

<400> SEQUENCE: 1
atcccaaatg acaaaaataa caatatagaa aatacaaaaa caaaaacaaa atatgaaaga      60
gtgttatggt ggggacgtta attgactcaa ttacgttcat acattataca cacctactcc     120
catcacaatg aaacgcttta ctccaaaaaa aaaaaaaaaa ccactcttca aaaaatctcg     180
tagtctcacc aaccgcgaaa tgcaactatc gtcagccacc agccacgacc acttttacca     240
ccgtgacgtt gacgaaaacc aaagaaattc accaccgtgt taaaatcaaa ttaaaaataa     300
ctctcttttt gcgacttaaa ccaaatccac gaattataat ctccaccact aaaatccatc     360
actcactctc catctaacgg tcatcattaa ttctcaacca actccttctt tctcactaat     420
tttcattttt tctataatct ttatatggaa gaaaaaaaga aactagctat ctctatacgc     480
ttacctacca acaaacacta ccaccttatt taaaccaccc ttcattcatc taattttcct     540

<210> SEQ ID NO 2
<211> LENGTH: 2247
<212> TYPE: DNA
<213> ORGANISM: Caenorhabditis elegans

<400> SEQUENCE: 2
aatatgggtg gattcttgtc tcatctgact cctgaacaga atgttgaagc attgaaagct      60
tcttgtggtc ccgtaagagg aaacatttat aaacatgtaa gaatttaaaa tttagtttaa     120
tatctcaaag atcattgttt ttaggatgat gtgattgttg atgggtacct cgggatcccg     180
tatgcgaaac caccagtcgg cgaacttcga tttaagaagc cagtaaccgt tgatgtttgg     240
acagagatca aagattgtta taaatatgga ccagcttgtg tacagactgg tggatttgag     300
caggttagtt gctcaattta cagcaagttc atttagttgt tgtttttaaa aattgaaaat     360
taaagcgaaa tccatctgaa aattgtgttt tatttcagat tgctggtcca agaactccaa     420
ctccggaaga ggctggttgt ctcacactga atgtgttcac acccagaaat gcatcttctg     480
aatttgcaag ttcacctgaa atttcagaaa taaaataaat ctagtttttt tttagaaaaa     540
tggacgaccg gttatggttt acattcatgg aggaggatac gagttgtgcg catcctctga     600
tttctgtgct tactcccttt ccgggttaga atcatattcg ataaagcaaa atatttgata     660 aggtttttatt tctgtcgttc gagagaatta tgatagtatg aactagcgaa aaaataaaac     720
aaacaatagt tcctgaatga ttatatttaa ttttcagaac tctcccactt aaagatgtcg     780
tggtagtttc tattaactac cgcctcggtg tgtttggatt cctcaccact ggagacaatg     840
```

```
tctgtcctgg aaattttggt ctttgggatc agactttggc tcttaaatgg gttcaaaaac    900
atatttcttc atttggaggt gatccaaatt gtgtgactgt ctttggacaa agtgcaggag    960
gagcaagtac tgatttatta tcattgagcc cacattcaag aggtttgagg ttttaaaata   1020
aaaataaaaa tactgtttaa attaactttc taaaataata aatttctaat attttcagat   1080
ttgttccagc gcttcattcc aatttccgga acggctcatt gtgactttgc cattagagca   1140
tctgaaaatc aagccaagat tttccgagaa tttgcagagt tcatggtttt tctggaaga   1200
gattcgtcag cactcttcaa gtggtaccaa gagcaatcgc cagaaactct gtcaaatgta   1260
aaaggataca aaaaatcgat ttctggattc ctcacattca ttcctaactt ggatggagat   1320
ttcttcccga aaccattgga tgagctaaga aaggaagctc caaagaagca aatgatgact   1380
ggagttactg agtatgaagg tcttatgtta gcatcaatga atccagcatt ttctcctgct   1440
gatgtcgggt tgacacttat gcctcaagga atttatggaa aagatgtggt tagcaatccg   1500
gatgaaattc agaagatttt ctatgaaaaa tacgtcgaag gagttgacaa atcagatgag   1560
ttggcgatga gaaagaaact atgtgaagct ctcggagatg aattttcaa cgtaggagtg   1620
attcaggcag ccaaaaatgc tgccaagcat ggaaatgagg tgtacttcta cactttcgaa   1680
tacgtgaatc cagatagttt tggaatgtgg gatggaatga tgccgttcaa gggtttgtaa   1740
tcaggaagct gataatattt cattcgtttc ttttccagct gctgttcatt gcaccgagct   1800
cagatatctt ctcggtgaag gagtttacag caagttcgaa ccaacagagg aagatcggaa   1860
agttatggag actacgacta cattattttc aaattttgcc aaatatgggt gagaaaggaa   1920
ttcagaatta tgaaattgag ttttttttaaa gaaatccaaa tggaaaagga gccaccgccg   1980
agatatggga gaaatacagc ttaaaccgtc cagagagaca ttacagaatt tcttatccaa   2040
aatgtgaaat gagagatgtt tatcacgagg gtagaattca gtttttggag aaaatcgatg   2100
gagatagtga taagtatcaa gaattggtct atggaaagaa gaagtcggca agatttaat   2160
tttttttgaa gaaaaaaaat tgcaaatgtt cgaataattt tattacaatg taaaataaat   2220
attgtatcaa ttagtttaat aaagtaa                                       2247
```

<210> SEQ ID NO 3
<211> LENGTH: 987
<212> TYPE: DNA
<213> ORGANISM: Escherichia coli

<400> SEQUENCE: 3

```
atgtcgcacg tagagttaca accgggtttt gactttcagc aagcaggtaa agaagtcctg     60
gcgattgaac gtgaatgcct ggcggagctt gatcaataca tcaatcagaa tttcacgctt    120
gcctgtgaaa agatgttctg tgtaaagggg aagttgtcg tcatggggat gggaaaatcg    180
gggcatattg ggcgaaaaat ggcggcaacg tttgccagca ccggtacacc ttcattttc    240
gtccatcctg gtgaagccgc gcatggtgat ttaggcatgg ttaccccaca ggatgtggtg    300
attgctatct ctaactctgg tgaatccagc gaaatcacgg ccttaattcc agtgcttaag    360
cgtcttcacg taccgttaat ctgcatcacc ggtcgcccgg agagcagcat ggcgcgcgcc    420
gcagatgtgc atctgtgtgt taagtagcg aaagaagcct gtccgttagg gctggcaccg    480
accagcagca ccaccgccac gctggttatg ggcgatgccc tcgctgtcgc gctgttaaaa    540
gcacgcggct ttactgctga agattttgcg ctctcacacc caggcggcgc actgggtcgt    600
aaacttctgc tgcgcgtaaa cgatattatg catacgggcg atgagatccc gcatgttaag    660
```

```
aaaacggcca gtctgcgtga cgcgttgctg aagttaccc gcaaaaatct tggtatgact      720
gtcatttgcg atgacaatat gatgattgaa ggcatcttta ccgacggtga tttacgccgt      780
gtcttcgata tgggcgtgga tgttcgtcag ttaagtattg ccgatgtgat gacgccgggg      840
ggaatacgtg tgcgccctgg cattctggcc gttgaggcac tgaacttaat gcagtcccgc      900
catatcacct ccgtgatggt tgccgatggc gaccatttac tcggtgtgtt acatatgcat      960
gatttactgc gtgcaggcgt agtgtaa                                         987

<210> SEQ ID NO 4
<211> LENGTH: 1497
<212> TYPE: DNA
<213> ORGANISM: Bacillus halodurans

<400> SEQUENCE: 4
atgaagcaat caattaaagt ctatacagat cttgaacatg ggaaaattag caagcatatt       60
tatggtcatt tttcagagca tttaggcagg tgcatttatg aaggattgtg ggttggagag      120
gactcaccaa tcccaaatac agaggggatc cgcaatgatg tactagggc attacaagag       180 ttaaacatcc cggtcctacg ctggccaggg ggctgctttg ccgatgagta ccattggaaa      240
gatggtgtgg ggccaaggga gaaccggaag cgaatggtga cacccattg gggcggtgtt       300 gtcgaaaata atcatttcgg cacgcatgag tttatgagat tatgtgagct cctcggcgcc      360
gaaccttaca tttgtggaaa tgtcggcagt ggtaccgttc aagaaatgca agaatggggtt    420 gaatatatga catttgatgg ggaatcgcca atggccaatt ggcgcacaga aaatgggcga      480
gaagagcctt gggctttaaa atattttggt gttggaaatg aaaactgggg ctgcgggggg      540
catatgcgtc ctgaatacta tgcggatctt taccgacgct atcaaaccta tgtccgtaac      600
tatggagaca acaaaattta taagattgct ggtggggcca atgtagacga ctaccgttgg      660
actgaggtgt tgatgcgaga agcggctcat cttatggatg gattgagcct gcattattac      720
acggttccag gggattttg ggaaaataaa gggtcggcct tagacgatcg tgaatctgaa       780
tggtttaaaa cgttgaaaaa gtcgttccga atggatgaat tattgacgaa gcattcgaca      840
attatggacc gttatgatcc tgaaaagcga gtcggcttaa ttgtcgatga atggggtaca      900
tggtttgatg tggagccagg tacaaatcca ggcttccttt atcaacaaaa tacgatccgt      960
gatgcgttag tggctggcgt tcattttcac attttccatg agcataacga ccgggttcat     1020
atggcgaaca tcgcacaaat ggtcaatgtt ttgcaggcga tggtgttgac ggaaggggag     1080
cagatgcttt taacgccaac ctatcatgta tttaacatgt ataaagttca tcaagatgca     1140
acgagacttg aagtaaatgc agacgtggga acttacaagt tcggagatga tgaacttcca     1200
gcggtaaccg tttctgcatc gaaggataac gaaggtgcca ttcacgtaag tgtttgtcat     1260
ttagatcctc atcgtgatac agatcttaca cttaagctaa atgggctaaa caagtcgttg     1320
tcagcatcat ctgtttcagg agaactatta acagcaaatg aattaaatgc ccacaatacg     1380
tttgaacgac cgaatgaggt ggagcctgtt ccgtatgagc cagcttctgt aagcggacat     1440
gagatggagc taaaggttcc agcatcatct gtactccgtg tgacaattag accataa        1497

<210> SEQ ID NO 5
<211> LENGTH: 1533
<212> TYPE: DNA
<213> ORGANISM: Abies grandis

<400> SEQUENCE: 5
tcattgcagg tctcctatgc tcgcggccag ccgggcgaga ctcttccgct cgccgaggat       60
```

```
ggccgccgcg ctggcgatgt cgggagccag ccagcggtcg gtgtcgtacg cgggcacgcg      120
ctcgcgcagg atgccccagg ccgccgcggt gccctggccg aagcgttgcg gggcgaggaa      180
ttcgaaggcc tgggcggcca gcaggtactc gatggcgagg atccgccgga ggttctccag      240
ggccctgcca agcttgagcg cggcactggt gccgaggctc agtggtcct cctggagcgc       300 cgaggtgacg aagttgtcga ccaccgccgg ctgcgccagc tggcggttct cgccggccag      360
ggaggcggcg acgtactggg tgatcatcat ccccgagttg actcccggct gcccaccag      420 gaacgccggc aggccgctga ccagcgggtt gaccaggcga tccaggcgcc gctcggcgac      480
cccgcccagc tcggccacgg cgatcgccag caggtcggcg ccatcgcca ccgattcgcc       540 gtggggattg gcctgggata ccacccggta ggcttccggc gtacccagca gcagcgggtt     600
gtcggtggcc gagttgagtt cggtctctat ctgccgcgcc gcgtgggcca actggtcacg      660
gcaggcgcca tggatctgcg gtatcgagcg gatgctcagg gcatcctggg tgcggatgcc     720
gcgggcgttc tccagtacct ggctgccagc cagcaaggct cgcagattgg cggcgacccg     780
ctgcatcccg ggatgcggct tgagcgcaac gatctcggcg tcgaacgccg ccagttggcc     840
gcgcagggcc tcgaagctca tcgccccgat cacgtcggcc cactgcgcca ggcgctgcgc     900
gtcgtccagg ccaggcagg cgaggccggt catgcacggc gtgccgttga ccaggcagag     960
cccgtccttg gctcccaggc gcaccgtcgc caggccttcc gccgcaacg cggcggcggc      1020 cggcacgacg ctgccgcggt agctgacctc gccgatgccg agcagggcga tgccgacgtg     1080
cgccatgtgg gtcaggtagc ccaccgagcc ctgggccggc acctgcgggg taatgccgtg    1140
gttgagcagc gccagcagtc cttccaccag cgaacggtcg agcccggact tgccctggct     1200
gtagttggcg acggcggcac agatgatcgc ccgggtctgt tcgtcgcgca gcggctcgcc    1260
gaccccgcag gcatggctga gcaaggtgtt gcgcgacagc tcggcgagct gctcgccttc    1320
cagcaggacg tcgcacagcg cgccgaggcc ggtactgatg ccgtaggcac gctcgccgtt    1380
ggcgacgata cggcagacga tggcgcgggc gttgtcgatc cgtgcccagg ccgccgccga    1440
cagttccagg cgcgcaccgt gccgggccac cgcgaccagt tcctgccaac gcagcgggcc    1500
gtcgccgaac acgacgctcg gtaggtcgct cat                                  1533

<210> SEQ ID NO 6
<211> LENGTH: 2730
<212> TYPE: DNA
<213> ORGANISM: Arabidopsis thaliana

<400> SEQUENCE: 6
caacaacact aacattgtcc ttcttattta aacgtctctt ctctcttctt cctcctcaga      60
aaaccaaaaa ccaccaacaa ttcaaactct ctctttctcc tttcaccaaa caatacaaga    120
gatctgatct cattcaccta aacacaactt cttgaaaacc aatggatcaa atcgaagcaa    180
tgttgtgcgg cggaggagag aagacaaaag tggcggttac tacgaagact ttggcagatc     240
cattgaattg gggtttagca gcggatcaaa tgaaaggaag tcatttagat gaagtgaaga    300
agatggtcga agagtatcgt agaccagtcg tgaatcttgg cggagaaaca ctgacgatcg    360
gacaagttgc tgccatctcc accgtaggag gcagcgttaa ggttgagtta gcggagactt     420
caagagccgg tgtgaaagct agcagtgatt gggttatgga gagcatgaac aaaggtactg    480
acagttacgg agtcaccacc ggctttggtg ctacttctca ccggagaacc aaaaacggca    540
ccgcattaca aacagaactc attaggtaat taattaaatc ctatacctta tattatataa     600
```

```
ctaattaata attagagaac tcattaggaa tgtgatcaga gaaataaata aattagtggc    660
ttaagtggat aacgcatact cacgagtata caatttgcat gggagatata ccgggtcggt    720
gataccggtc gggtcgggtc tattttaatt aattaaagtt tatttccgat ttcagatttt    780
tgaacgccgg aatattcgga aacacgaagg agacatgtca cacactgccg caatccgcca    840
caagagccgc catgctcgtc agagtcaaca ctcttctcca aggatactcc gggatccgat    900
tcgagatcct cgaagcgatt acaagtctcc tcaaccacaa catctctccg tcactacctc    960
tccgtggaac cattaccgcc tccggcgatc tcgttcctct ctcttacatc gccggacttc   1020
tcaccggccg tcctaattcc aaagccaccg gtcccgacgg tgaatcgcta accgcgaaag   1080
aagcttttga gaaagccgga atcagtactg gattcttcga tttacaacct aaggaaggtt   1140
tagctctcgt taatggcacg gcggttggat ctggaatggc gtcgatggtt ctattcgaag   1200
cgaatgtcca gcggtgttta gcggaggttt tatcagcgat cttcgcggag gttatgagcg   1260
ggaaacctga gtttaccgat catctgactc atcgtttaaa acatcatccc ggacaaatcg   1320
aagcggcggc gataatggag cacatactcg acggaagctc atacatgaaa ttagctcaaa   1380
aggttcacga gatggatcca ttgcagaaac caaaacaaga tcgttacgct cttcgtacat   1440
ctcctcaatg gctaggtcct caaattgaag taatccgtca gctacgaaa tcgatagagc   1500 gtgaaatcaa ctccgttaac gataatccgt tgatcgatgt ttcgaggaac aaggcgattc   1560
acggtggtaa cttccaagga acaccaatcg gagtttctat ggataacacg agattggcga   1620
ttgctgcgat tgggaagcta atgtttgctc aattctctga gcttgttaat gatttctaca   1680
acaatggact tccttcgaat ctaactgctt cgagtaatcc aagtttggat tatggattca   1740
aaggagcaga gattgctatg gcttcttatt gttctgagct tcaatacttg gctaatccag   1800
tcacaagcca tgttcaatca gctgagcaac ataatcaaga tgtgaactct cttggtttga   1860
tctcgtctcg taaaacatct gaagctgtgg atattcttaa gctaatgtca caacgttcc   1920 ttgtggggat atgtcaagct gttgatttga gacatttgga ggagaatctg agacaaactg   1980
tgaagaacac agtttctcaa gttgctaaga agtgttaaac cactggaatc aacggtgagt   2040
tacatccgtc aaggttttgc gagaaggact tgcttaaggt tgttgatcgt gagcaagtgt   2100
tcacgtatgt ggatgatcct tgtagcgcta cgtacccgtt gatgcagaga ctaagacaag   2160
ttattgttga tcacgctttg tccaacggtg agactgagaa gaatgcagtg acttcgatct   2220
ttcaaaagat tggagctttt gaagaggagc ttaaggctgt gcttccaaag gaagttgaag   2280
cggctagagc ggcttatggg aatggaactg cgccgattcc taaccggatt aaggaatgta   2340
ggtcgtatcc gttgtatagg ttcgtgaggg aagagcttgg aacgaagttg ttgactggag   2400
aaaaggttgt gtctccggga gaggagtttg ataaggtctt cactgctatg tgtgaaggta   2460
aacttattga tccgttgatg gattgtctca aggaatggaa cggagctccg attccgattt   2520
gctaagagag cattcctctg tttctgttct gtgttttgt gttttgtttc aattttaatt   2580
ttgctgtgtt aatgtttgaa ttgagttttt gattgtaatg tgaatggtgt cacaccttgt   2640
atgatatata tgatataaaa acttacgtgt aaaactcgtt gttaacttgt tacttttttat   2700 gttggtaaat gtggatttga caccgttgac                                   2730
```

<210> SEQ ID NO 7  
<211> LENGTH: 2031  
<212> TYPE: DNA  
<213> ORGANISM: Selaginella moellendorffii

<400> SEQUENCE: 7

```
atgtcgggta gccacctcga ggaggtccgc gagatggtcc acaccgtcta cggcgccgcc    60
aagcccagct tctcgatcga gggcaccacg ctcaccatcg cccaggtggc ggcggtggcc   120
aagcgcggcg cccaggtacg cttggattcc gccgccgcca agaagagggt ggacgagagc   180
tccaactggg tactcgacaa tgcgatgaag gggaccgaca tctacggtgt cacgactgga   240
ttcggcgcca cctcccaccg ccggatcaac cagggcgtgg ggctccagcg cgagctcatc   300
cgcgtcctca cgccgggat cttcagcgac gacgattcga ccaacgttct cccgctggcc    360
ttcgcgcgcg ccgcgatgct ggtgcgcacc aacacgctcc tccagggcta ctcgggcatc   420
cggtggggaga tcctgtccgc catggagaag ctcgtcaact cgggcatcgt ggcgcggatc   480
ccactccgcg ggacgatcac tgcctccggc gatctcgtcc ctctcagcta cattgccggg   540
ctgctcagcg gccgatccaa cgtgcgcgcc gtcttgccgg gtgggaaggt cgtcaccagc   600
gccgaggcgc tcaagctcgt cggcgtggag cagccgttcg agctccagcc caaggaaggc   660
ttcgccatcg ttaacggcac ggcagtcggc gcggcgtgg cctccatcgc ctgcttcgac    720
gccaacgtcc tggcgctcct ggccgagatc ctgtccgcga tgttctgcga ggcgatgcaa   780
ggcaagcccg agttcacgga tccgctgacg cacaagctca agcaccaccc cggccagatc   840
gaggccgccg ccatcatgga acatgtcctc gccgggagct cctacatgaa agccgccgcc   900
aagctccacg agaccgactc cctcaagaag cccaagcagg accgctacgc gctgcgcacc   960
tccccgcagt ggctcggccc ccagatcgaa gtcatccgcc acgccactca ctccatccag  1020
cgcgagatca actccgtgaa tgacaacccg atcatcgatg ttgctcgcga caaggccctc  1080
cacggcggga acttccaggg gacgcccatc ggtgtgtcca tggataactt gcgcttggcg  1140
gtggcggcca tcgggaagct catgttcgcg cagttctcgg agctcgtcaa tgacttctac  1200
aacaacggcc tgccttccaa cttgagcggc ggatccaacc cgagcttgga ctatggtttc  1260
aaaggtgccg agatcgccat ggcctcgtac acctcggagc tccagtacct ggccaacccg  1320
gtcaccaccc acgtccagag cgccgagcag cacaaccagg acgtgaactc tctcggcctc  1380
gtctccgctc gcaagacggt ggaagctctc gacatcctca agctcatgtc gtcgacgtat  1440
ctggtggcat tgtgccaggc catcgacctc cgccacctcg aggagaactt gcaagccacc  1500
gtgaagcaga ccgtctctca cgccgctaag aacacggtca ccaccggagc tgccggagcg  1560
ctgctgccgt cgcgcttctg cgagaaggag ctcctgtccg tggtggacaa ccagcacgtc  1620
ttcacctaca tcgatgatcc ggccagcgct ggatacccgc tcatgcagaa gctccgccag  1680
gttctcgtcg agcacgcctt gaagaacatc ggggacgaga gctcctcggt gttgcacaag  1740
atcgggctgt tcgaggagga gctcaaggcg gcgttgagtg tcgaggtccc ggcggccagg  1800
gaggcgtacg agagcggtaa gcggtgctg ccaaaccgga tcttcgactg tgcctcggcg   1860
ccgctgtatg agtttgtgag gaaaggtgct ggaactgcgc tgctcatggg gaccaagagt  1920
ggaacgcccg gcgaggactt caccaaagtc tacgatgcca tctgccaggg gaagcttgtt  1980
gctcccttgt tgaagtgtct cgatggctgg tccggaacgc ccagttttg a             2031
```

<210> SEQ ID NO 8
<211> LENGTH: 29
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<222> LOCATION: (13)..(15)

```
<223> OTHER INFORMATION: n is a, c, g, or t
<220> FEATURE:
<221> NAME/KEY: misc_feature
<222> LOCATION: (18)..(20)
<223> OTHER INFORMATION: n is a, c, g, or t

<400> SEQUENCE: 8
tctagagaaa gannngannn tactagatg                                              29

<210> SEQ ID NO 9
<211> LENGTH: 13
<212> TYPE: DNA
<213> ORGANISM: Artificial sequence
<220> FEATURE:
<223> OTHER INFORMATION: Synthetic construct

<400> SEQUENCE: 9
tcacacagga aag                                                               13

<210> SEQ ID NO 10
<211> LENGTH: 129
<212> TYPE: DNA
<213> ORGANISM: Artificial sequence
<220> FEATURE:
<223> OTHER INFORMATION: Synthetic construct

<400> SEQUENCE: 10
ccaggcatca ataaaacga aaggctcagt cgaaagactg ggcctttcgt tttatctgtt            60
gtttgtcggt gaacgctctc tactagagtc acactggctc accttcgggt gggcctttct          120
gcgtttata                                                                  129

<210> SEQ ID NO 11
<211> LENGTH: 1362
<212> TYPE: DNA
<213> ORGANISM: Artificial sequence
<220> FEATURE:
<223> OTHER INFORMATION: Synthetic construct

<400> SEQUENCE: 11
tggctgcgtc tggtgggacc gttgtatacg ccggtagtgg tttgcggggc tacggcgagt           60
tggtcatcat caaacacaac gagacctacg tgagtgccta cggtcacaac cgcaggctgc          120
tggtgcggga agggcaacag gtcaaggtag ggcaatcgat tgccgagatg ggctccacag          180
gaaccgatcg ggtgaagctg cacttcgaga ttcgccgcca gggtaagcct gtcgatccac          240
tgcaatattt gccacgtcgc tgaccgggag ttcgcccgcc cacatcatgt aggtgagcgg          300
gtccgggcgt gtccagcggg aaaggaatcg cccgggcttg agtcgaactc atgcaaggga          360
taacgacatg gcactcaaaa agaagggcc ggagtttgac cacgatgatg aagtgctcct           420
cctggagccc ggcatcatgc tggacgagtc gtctgccgac gagcagcctt ctccccgggc          480
aactccaaaa gccaccactt ccttctcttc caaacaacac aagcacatcg actacacgcg          540
cgcgttggac gcaacgcagc tgtatctcaa cgaaatcggt ttctcgcccc tgttgacgcc          600
cgaagaggaa gtccacttcg ctcgtctggc gcagaagggc gatcccgctg gtcggaagcg          660
gatgatcgag agcaacctgc ggttggtggt gaagatcgcc cggcgctatg tcaatcgcgg          720
actgtccctg ctcgacctga tcgaggaagg caacctaggc ctgatccgcg ccgtggagaa          780
gttcgatccg gagcgcggat tccggttctc gacctacgcc acctggtgga tccgccagac          840
catcgagcgg gccatcatga accagacccg gaccattcgc ttgccgatcc atgtggtcaa          900
ggagctcaac gtctacctgc gtgcggcgcg ggaactgacc cacaagctcg accacgaacc          960
```

```
ttcacccgaa gaaatcgcca acctgctgga gaagccggtc gccgaggtca agcgcatgct    1020
cggcctgaac gaacgggtga cttcggtaga cgtctctctt ggtccggact cggacaagac    1080
cctgctggat acgctcaccg acgatcgccc caccgatccg tgcgagctgc tgcaggatga    1140
cgatctcagc gaaagcagct gacgaactc accgacaagc agcgtgaggt ggtgattcgc     1200
cgcttcggct tgcgcggtca cgaaagcagc acgctggaag aggtcggcca ggaaatcggc    1260
ctgacccgcg agcgggttcg tcagatccag gtcgaggcgc tgaagcgcct gcgggagatt    1320
ctggagaaga atggcctgtc gagtgacgcg ctgttccagt ga                       1362

<210> SEQ ID NO 12
<211> LENGTH: 18
<212> TYPE: DNA
<213> ORGANISM: Artificial sequence
<220> FEATURE:
<223> OTHER INFORMATION: Synthetic construct

<400> SEQUENCE: 12
cccgccgcca ccatggag                                                  18

<210> SEQ ID NO 13
<211> LENGTH: 76
<212> TYPE: RNA
<213> ORGANISM: Artificial sequence
<220> FEATURE:
<223> OTHER INFORMATION: Synthetic construct

<400> SEQUENCE: 13
ugcuuaaggc cuaaaacaua ccagaucgcc acccgcgcuu uaaucuggag aggugaauac    60
gaccaccuag gccaaa                                                    76

<210> SEQ ID NO 14
<211> LENGTH: 111
<212> TYPE: DNA
<213> ORGANISM: Artificial sequence
<220> FEATURE:
<223> OTHER INFORMATION: Synthetic construct

<400> SEQUENCE: 14
cgcgcgtcgt gcgagtggct cgatcgatct cacgctcgat cgcgtctgag aacacatcgc    60
tggaacttga ctcaggataa tacctgcgta aggaacgacc gcggcatcgc g             111

<210> SEQ ID NO 15
<211> LENGTH: 979
<212> TYPE: DNA
<213> ORGANISM: Artificial sequence
<220> FEATURE:
<223> OTHER INFORMATION: Synthetic construct

<400> SEQUENCE: 15
tccctatcag tgatagagat tgacatccct atcagtgata gagatactga gcactactag    60
agaaagagga gaaatactag atggtgagca agggcgagga gctgttcacc ggggtggtgc    120
ccatcctggt cgagctggac ggcgacgtga acggccacaa gttcagcgtg tccggcgagg    180
gcgagggcga tgccacctac ggcaagctga ccctgaagtt catctgcacc accggcaagc    240
tgcccgtgcc ctggcccacc ctcgtgacca ccctgacctg gggcgtgcag tgcttcagcc    300
gctaccccga ccacatgaag cagcacgact tcttcaagtc cgccatgccc gaaggctacg    360
tccaggagcg caccatcttc ttcaaggacg acggcaacta caagacccgc gccgaggtga    420
```

```
agttcgaggg cgacaccctg gtgaaccgca tcgagctgaa gggcatcgac ttcaaggagg    480
acggcaacat cctggggcac aagctggagt acaactacat cagccacaac gtctatatca    540
ccgccgacaa gcagaagaac ggcatcaagg ccaacttcaa gatccgccac aacatcgagg    600
acggcagcgt gcagctcgcc gaccactacc agcagaacac ccccatcggc gacggccccg    660
tgctgctgcc cgacaaccac tacctgagca cccagtccgc cctgagcaaa gaccccaacg    720
agaagcgcga tcacatggtc ctgctggagt tcgtgaccgc cgccgggatc actctcggca    780
tggacgagct gtacaagagg cctgctgcaa acgacgaaaa ctacgcttta gtagcttaat    840
aatactagag ccaggcatca aataaaacga aaggctcagt cgaaagactg ggcctttcgt    900
tttatctgtt gtttgtcggt gaacgctctc tactagagtc acactggctc accttcgggt    960
gggcctttct gcgtttata                                                 979
```